US006548650B1

(12) United States Patent
Fisher

(10) Patent No.: US 6,548,650 B1
(45) Date of Patent: Apr. 15, 2003

(54) NUCLEIC ACID ENCODING MELANOMA DIFFERENTIATION ASSOCIATED GENE-9

(75) Inventor: Paul B. Fisher, Scarsdale, NY (US)

(73) Assignee: Trustees of Columbia University in the City of New York, New York, NY (US)

( * ) Notice: Subject to any disclaimer, the term of this patent is extended or adjusted under 35 U.S.C. 154(b) by 0 days.

(21) Appl. No.: 09/345,883

(22) Filed: Jun. 30, 1999

Related U.S. Application Data

(63) Continuation of application No. PCT/US97/24030, filed on Dec. 30, 1997, which is a continuation-in-part of application No. 08/774,465, filed on Dec. 30, 1996, now Pat. No. 6,071,696.

(51) Int. Cl.[7] .......................... C07H 21/04; C12Q 1/68; G01N 33/53; G01N 33/48; A61K 38/00
(52) U.S. Cl. .......................... 536/22.1; 435/6; 435/7.2; 435/7.23; 436/63; 436/64; 530/300
(58) Field of Search .......................... 435/6, 7.2, 7.23; 436/63, 64; 530/300; 536/22.1

(56) References Cited

PUBLICATIONS

Jiang et al., "Subtraction Hybridization identifies a novel ——", *Oncogene*, vol. 11, pp. 2477–2486, Oct. 1995.*
Lin et al. "Characterization of a Novel Melanoma Differentiation Associated Gene ——", *Molecular and Cellular Differentiation*, vol. 4 (4), pp. 317–333, Apr. 1996.*
Lin et al., "Melanoma Differentiation Associated Gene . . . ", *Gene* vol. 207, pp. 105–110, 1998.*
Groofjans et al., "Syntenin, a PDZ Protein . . . ", Proc. Natl. Acad. Sci. USA, vol. 94, pp. 13683–13688, Dec. 1997.*
A copy from the NCBI website for a "GENBANK Deposit", 3 pages, Revised Oct. 24, 2001.
Duguid, J.R., et al. (1988) Isolation of cDNAs Of Scrapie–Modulated RNAs By Subtractive Hybridization Of A cDNA Library, *Proc. Natl. Acad. Sci., USA*, 85:5738–5742.
Fisher, P.B. et al. (1986) Effect Of Recombinant Human Fibroblast Interferon And Mezerein On Growth, Differentiation, Immune Interferon Binding And Tumor Associated Antigen Expression In Human Melanoma Cells, *Anticancer Research*, 6(4):765–774.
Hara, E., et al. (1993) DNA—DNA Substractive cDNA Cloning Using Oligo(dT)$_{30}$–1 latex And PCR: Identification Of Cellular Genes Which Are Overexpressed In Senescent Human Diploid Fibroblasts, *Anal. Biochem.*, 214:58–64.
Hara, E., et al. (1991) Subtractive cDNA Cloning Using Oligo(dT)$_{30}$–latex and PCR: Isolation of cDNA Clones Specific To Undifferentiated Human Embryonal Carcinoma Cells, *Nucleic Acids Research*, 19(25):7097–7104.
Herfort, M.R., and Garber, A.T. (1991) Simple And Efficient Subtractive Hybridization Screening, *BioTechniques*, 11(5)598–603.

Jiang, H., et al. (1994) Induction of Differentiation in Human Promyelocytic HL–60 Leukemia Cells Activates p21, WAF1/CIP1, Expression in the Absence of p53, *Oncogene*, 9:3397–3406.
Jiang, H. et al. (1995) Subtraction Hybridization Identifies A Novel Melanoma Differentiation Associated Gene, mda–7, Modulated During Human Melanoma Differentiation, Growth And Progression, *Oncogene*, 11:2477–2486.
Jiang, H. et al. (1993) Use Of A Sensitive And Efficient Subtraction Hybridization Protocol For The Identification Of Genes Differntially Regulated During The Induction Of Differentiation In Human Melanoma Cells, *Molecular And Cellular Differentiation*, 1(3):285–299.
Jiang, H. et al. (1994) A Molecular Definition Of Terminal Cell Differentiation In Human Melanoma Cells, *Molecular And Cellular Differentiation*, 2(3):221–239.
Lee, S.W., et al. (1991) Positive Selection Of Candidate Tumor–Suppressor Genes By Subtractive Hybridization, *Proc. Natl. Acad. Sci., USA*, 88:2825–2829.
Maniatis, T., et al. (1982) Strategies For cDNA Cloning, *Molecular Cloning: A Laboratory Manual*, Cold Spring Harbor Laboratory, pp. 224–228.
Rubenstein, J.L.R., et al. (1990) Subtractive Hybridization System Using Single–Stranded Phagemids With Directional Inserts, *Nucleic Acids Research*, 18(16):4833–42.
Travis, G., et al. (1988) Phenol Emulsion–Enhanced DNA–Driven Subtractive _ cDNA Cloning: Isolation Of Low–Abundance Monkey Cortex–Specific mRNAs, *Proc. Natl. Acad. Sci., USA*, 85:1696–1700.
Sive, H.L., et al. (1988) A Simple Subtractive Hybridization Technique Employing Photoactivatable Biotin And Phenol Extraction, *Nucleic Acids Research*, 16(22):10937.
Wieland, I., et al. (1990) A Method For Difference Cloning: Gene Amplification Following Subtractive Hybridization, *Proc. Natl. Acad. Sci., USA*, 87:2720–2724.

* cited by examiner

*Primary Examiner*—W. Gary Jones
*Assistant Examiner*—Arun Kr. Chakrabarti
(74) *Attorney, Agent, or Firm*—Baker Botts, LLP

(57) ABSTRACT

This invention provides a method for producing a temporally paced subtracted cDNA library comprising: a) isolating temporally spaced RNAs from cells; b) generating cDNA inserts from the RNAs isolated from step (a); c) producing a temporally spaced cDNA library having clones containing the cDNA inserts generated from step (b); d) producing double stranded cDNA inserts from the temporally spaced cDNA library; e) denaturing the double stranded cDNA inserts; f)contacting the denatured double stranded cDNA inserts produced in step (e) with single-stranded DNAs from another cDNA library under conditions permitting hybridization of the single-stranded DNAs and the double-stranded cDNA inserts; g) separating the hybridized cDNA inserts from the unhybridized inserts; h) generating a cDNA library of the unhybridized inserts, thereby generating a temporally spaced subtracted cDNA library.

9 Claims, 10 Drawing Sheets mda-9

Ubiquitin

FIGURE 6C

Human RNA Master Blot Code

| | 1 | 2 | 3 | 4 | 5 | 6 | 7 | 8 |
|---|---|---|---|---|---|---|---|---|
| A | whole brain | amygdala | caudate nucleus | cerebellum | cerebral cortex | frontal lobe | hippocampus | medulla oblongada |
| B | occipital lobe | putamen | substantia nigra | temporal lobe | thalamus | sub-thalamic nucleus | spinal cord | |
| C | heart | aorta | skeletal muscle | colon | bladder | uterus | prostate | stomach |
| D | testis | ovary | pancreas | pituitary gland | adrenal gland | thyroid gland | salivary gland | mammary gland |
| E | kidney | liver | small intestine | spleen | thymus | peripheral leukocyte | lymph node | bone marrow |
| F | appendix | lung | trachea | placenta | | | | |
| G | fetal brain | fetal heart | fetal kidney | fetal liver | fetal spleen | fetal thymus | fetal lung | |
| H | yeast total RNA 100ng | yeast tRNA 100ng | E coli tRNA 100ng | E coli DNA 100ng | poly r(A) 100ng | human $C_0t$ 1 DNA 100ng | human DNA 100ng | human DNA 500ng |

FIGURE 7

```
CCTCAGAAGTCCGTGCCAGTGACCGGAGGCGGCGGCGGCGAGCGGTTCCTTGTGGGCTAG        60
AAGAATCCTGCAAAAATGTCTCTCTATCCATCTCTCGAGGACTTGAAGGTAAACAAATTA       120
              M  S  L  Y  P  S  L  E  D  L  K  V  N  K  L
ATTCAGGCTCAAACTGCTTTTTCTGCAAACCCTGCCAATCCAGCAATTTTGTCAGAAGCT       180
 I  Q  A  Q  T  A  F  S  A  N  P  A  N  P  A  I  L  S  E  A
TCTGCTCCTATCCCTCACGATGGAAATCTCTATCCCAGACTGTATCCAGAGCTCTCTCAA       240
 S  A  P  I  P  H  D  G  N  L  Y  P  R  L  Y  P  E  L  S  Q
TACATGGGGCTGAGTTTAAATGAAGAAGAAATACGTGCAAATGTGGCCGTGGTTTCTGGT       300
 Y  M  G  L  S  L  N  E  E  E  I  R  A  N  V  A  V  V  S  G
GCACCACTTCAGGGGCAGTTGGTAGCAAGACCTTCCAGTATAAACTATATGGTGGCTCCT       360
 A  P  L  Q  G  Q  L  V  A  R  P  S  S  I  N  Y  M  V  A  P
GTAACTGGTAATGATGTTGGAATTCGTAGAGCAGAAATTAAGCAAGGGATTCGTGAAGTC       420
 V  T  G  N  D  V  G  I  R  R  A  E  I  K  Q  G  I  R  E  V
ATTTTGTGTAAGGATCAAGATGGAAAAATTGGACTCAGGCTTAAATCAATAGATAATGGT       480
 I  L  C  K  D  Q  D  G  K  I  G  L  R  L  K  S  I  D  N  G
ATATTTGTTCAGCTAGTCCAGGCTAATTCTCCAGCCTCATTGGTTGGTCTGAGATTTGGG       540
 I  F  V  Q  L  V  Q  A  N  S  P  A  S  L  V  G  L  R  F  G
GACCAAGTACTTCAGATCAATGGTGAAAACTGTGCAGGATGGAGCTCTGATAAAGCGCAC       600
 D  Q  V  L  Q  I  N  G  E  N  C  A  G  W  S  S  D  K  A  H
AAGGTGCTCAAACAGGCTTTTGGAGAGAAGATTACCATGACCATTCGTGACAGGCCCTTT       660
 K  V  L  K  Q  A  F  G  E  K  I  T  M  T  I  R  D  R  P  F
GAACGGACGATTACCATGCATAAGGATAGCACTGGACATGTTGGTTTTATCTTTAAAAAT       720
 E  R  T  I  T  M  H  K  D  S  T  G  H  V  G  F  I  F  K  N
GGAAAAATAACATCCATAGTGAAAGATAGCTCTGCAGCCAGAAATGGTCTTCTCACGGAA       780
 G  K  I  T  S  I  V  K  D  S  S  A  A  R  N  G  L  L  T  E
CATAACATCTGTGAAATCAATGGACAGAATGTCATTGGATTGAAGGACTCTCAAATTGCA       840
 H  N  I  C  E  I  N  G  Q  N  V  I  G  L  K  D  S  Q  I  A
GACATACTGTCAACATCTGGGACTGTAGTTACTATTACAATCATGCCTGCTTTTATCTTT       900
 D  I  L  S  T  S  G  T  V  V  T  I  T  I  M  P  A  F  I  F
GAACATATTATTAAGCGGATGGCACCAAGCATTATGAAAAGCCTAATGGACCACACCATT       960
 E  H  I  I  K  R  M  A  P  S  I  M  K  S  L  M  D  H  T  I
CCTGAGGTTTAAAATTCACGGCACCATGGAAATGTAGCTGAACGTCTCCAGTTTCCTTCT      1020
 P  E  V
TTGGCAACTTCTGTATTATGCACGTGAAGCCTTCCCGGAGCCAGCGAGCATATGCTGCAT      1080
GAGGACCTTTCTATCTTACATTATGGCTGGGAATCTTACTCTTTCATCTGATACCTTGTT      1140
CAGATTTCAAAATAGTTGTAGCCTTATCCTGGTTTTACAGATGTGAAACTTTCAAGAGAT      1200
TTACTGACTTTCCTAGAATAGTTTCTCTACTGGAAACCTGATGCTTTTATAAGCCATTGT      1260
GATTAGGATGACTGTTACAGGCTTAGCTTTGTGTGAAAACCAGTCACCTTTCTCCTAGGT      1320
AATGAGTAGTGCTGTTCATATTACTTTAGTTCTATAGCATACTGCATCTTTAACATGCTA      1380
TCATAGTACATTTAGAATGATTGCCTTTGATTTTTTTTTAAATTCTGTGTGTGTGTGTG      1440
TAAAATGCCAATTAAGAACACTGGTTTCATTCCATGTAAGCATTAAACAGTGTATGTAGG      1500
TTTCAAGAGATTGTGATGATTCTTAAATTTTAACTACCTTCACTTAATATGCTTGAACTG      1560
TCGCCTTAACTATGTTAAGCATCTAGACTAAAAGCCAAAATATAATTATTGCTGCCTTTC      1620
TAAAAACCCAAAATGTAGTTCTCTATTAACCTGAAATGTACACTAGCCCAGAACAGTTTA      1680
ATGGTACTTACTGAGCTATAGCATAGCTGCTTAGTTGTTTTTGAGAGTTTTTAGTCAACA      1740
CATAATGGAAACTTCTTTCTTCTAAAAGTTGCCAGTGCCACTTTTAAGAAGTGAATCACT      1800
ATATGTGATGTAAAAGTTATTACACTAAACAGGATAAACTTTTGACTCCCCTTTTGTTCA      1860
TTTGTGGATTAAGTGGTATAATACTTAATTTTGGCATTTGACTCTTAAGATTATGTAACC      1920
TAGCTACTTTGGGATGGTCTTAGAATATTTTTCTGATAACTTGTTCCTTTTCCTGACTCC      1980
TCCTTGCAAACAAAATGATAGTTGACACTTTATCCTGATTTTTTTCTTCTTTTTGGTTTA      2040
TGTCTATTCTAATTAAATATGTATAAATAAAAAAAAAAAAAAAAA                     2084
```

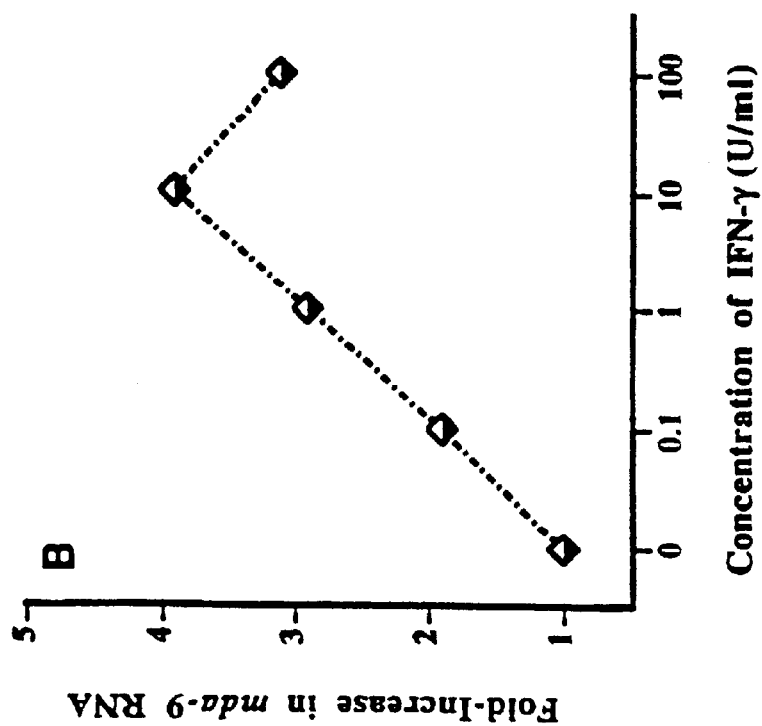
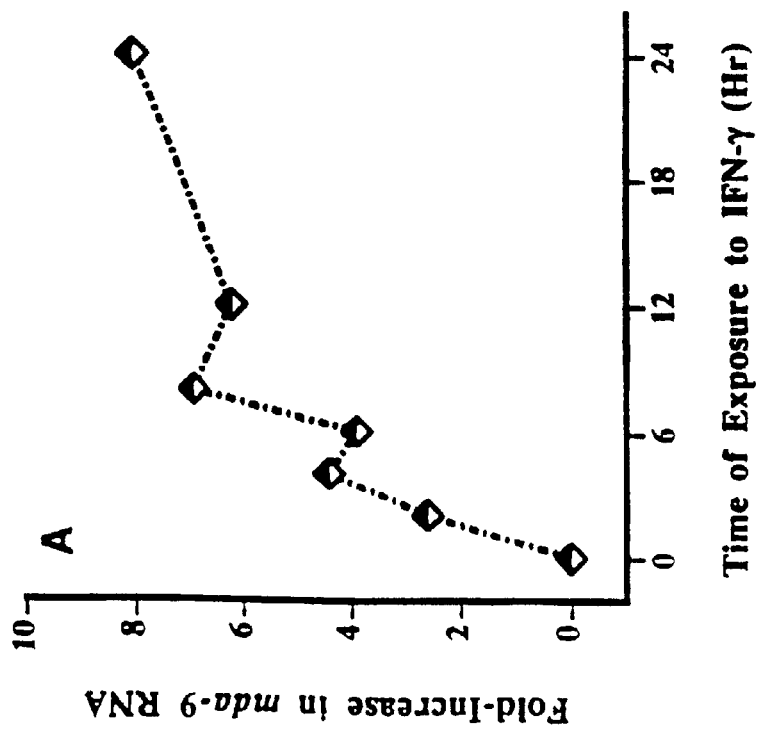
FIGURE 9A
FIGURE 9B

SEQUENCE LISTING (1) GENERAL INFORMATION:

(iii) NUMBER OF SEQUENCES: 2

(2) INFORMATION FOR SEQ ID NO: 1:

(i) SEQUENCE CHARACTERISTICS:
      (A) LENGTH: 2084 base pairs
      (B) TYPE: nucleic acid
      (C) STRANDEDNESS: single
      (D) TOPOLOGY: linear (ii) MOLECULE TYPE: DNA (genomic)

(ix) FEATURE:
      (A) NAME/KEY: CDS
      (B) LOCATION: 76..972

(xi) SEQUENCE DESCRIPTION: SEQ ID NO: 1:

```
CCTCAGAAGT CCGTGCCAGT GACCGGAGGC GGCGGCGGCG AGCGGTTCCT TGTGGGCTAG        60

AAGAATCCTG CAAAA ATG TCT CTC TAT CCA TCT CTC GAG GAC TTG AAG GTA       111
                Met Ser Leu Tyr Pro Ser Leu Glu Asp Leu Lys Val
                  1               5                  10

AAC AAA TTA ATT CAG GCT CAA ACT GCT TTT TCT GCA AAC CCT GCC AAT        159
Asn Lys Leu Ile Gln Ala Gln Thr Ala Phe Ser Ala Asn Pro Ala Asn
             15                  20                  25
```

-continued

```
CCA GCA ATT TTG TCA GAA GCT TCT GCT CCT ATC CCT CAC GAT GGA AAT     207
Pro Ala Ile Leu Ser Glu Ala Ser Ala Pro Ile Pro His Asp Gly Asn
         30                  35                  40

CTC TAT CCC AGA CTG TAT CCA GAG CTC TCT CAA TAC ATG GGG CTG AGT     255
Leu Tyr Pro Arg Leu Tyr Pro Glu Leu Ser Gln Tyr Met Gly Leu Ser
 45                  50                  55                  60

TTA AAT GAA GAA GAA ATA CGT GCA AAT GTG GCC GTG GTT TCT GGT GCA     303
Leu Asn Glu Glu Glu Ile Arg Ala Asn Val Ala Val Val Ser Gly Ala
                 65                  70                  75

CCA CTT CAG GGG CAG TTG GTA GCA AGA CCT TCC AGT ATA AAC TAT ATG     351
Pro Leu Gln Gly Gln Leu Val Ala Arg Pro Ser Ser Ile Asn Tyr Met
             80                  85                  90

GTG GCT CCT GTA ACT GGT AAT GAT GTT GGA ATT CGT AGA GCA GAA ATT     399
Val Ala Pro Val Thr Gly Asn Asp Val Gly Ile Arg Arg Ala Glu Ile
         95                 100                 105

AAG CAA GGG ATT CGT GAA GTC ATT TTG TGT AAG GAT CAA GAT GGA AAA     447
Lys Gln Gly Ile Arg Glu Val Ile Leu Cys Lys Asp Gln Asp Gly Lys
        110                 115                 120

ATT GGA CTC AGG CTT AAA TCA ATA GAT AAT GGT ATA TTT GTT CAG CTA     495
Ile Gly Leu Arg Leu Lys Ser Ile Asp Asn Gly Ile Phe Val Gln Leu
125                 130                 135                 140

GTC CAG GCT AAT TCT CCA GCC TCA TTG GTT GGT CTG AGA TTT GGG GAC     543
Val Gln Ala Asn Ser Pro Ala Ser Leu Val Gly Leu Arg Phe Gly Asp
                145                 150                 155

CAA GTA CTT CAG ATC AAT GGT GAA AAC TGT GCA GGA TGG AGC TCT GAT     591
Gln Val Leu Gln Ile Asn Gly Glu Asn Cys Ala Gly Trp Ser Ser Asp
            160                 165                 170

AAA GCG CAC AAG GTG CTC AAA CAG GCT TTT GGA GAG AAG ATT ACC ATG     639
Lys Ala His Lys Val Leu Lys Gln Ala Phe Gly Glu Lys Ile Thr Met
        175                 180                 185

ACC ATT CGT GAC AGG CCC TTT GAA CGG ACG ATT ACC ATG CAT AAG GAT     687
Thr Ile Arg Asp Arg Pro Phe Glu Arg Thr Ile Thr Met His Lys Asp
190                 195                 200

AGC ACT GGA CAT GTT GGT TTT ATC TTT AAA AAT GGA AAA ATA ACA TCC     735
Ser Thr Gly His Val Gly Phe Ile Phe Lys Asn Gly Lys Ile Thr Ser
205                 210                 215                 220

ATA GTG AAA GAT AGC TCT GCA GCC AGA AAT GGT CTT CTC ACG GAA CAT     783
Ile Val Lys Asp Ser Ser Ala Ala Arg Asn Gly Leu Leu Thr Glu His
                225                 230                 235

AAC ATC TGT GAA ATC AAT GGA CAG AAT GTC ATT GGA TTG AAG GAC TCT     831
Asn Ile Cys Glu Ile Asn Gly Gln Asn Val Ile Gly Leu Lys Asp Ser
            240                 245                 250

CAA ATT GCA GAC ATA CTG TCA ACA TCT GGG ACT GTA GTT ACT ATT ACA     879
Gln Ile Ala Asp Ile Leu Ser Thr Ser Gly Thr Val Val Thr Ile Thr
        255                 260                 265

ATC ATG CCT GCT TTT ATC TTT GAA CAT ATT ATT AAG CGG ATG GCA CCA     927
Ile Met Pro Ala Phe Ile Phe Glu His Ile Ile Lys Arg Met Ala Pro
270                 275                 280

AGC ATT ATG AAA AGC CTA ATG GAC CAC ACC ATT CCT GAG GTT TAA         972
Ser Ile Met Lys Ser Leu Met Asp His Thr Ile Pro Glu Val  *
285                 290                 295

AATTCACGGC ACCATGGAAA TGTAGCTGAA CGTCTCCAGT TCCTTCTTT GGCAACTTCT   1032

GTATTATGCA CGTGAAGCCT TCCCGGAGCC AGCGAGCATA TGCTGCATGA GGACCTTTCT   1092

ATCTTACATT ATGGCTGGGA ATCTTACTCT TTCATCTGAT ACCTTGTTCA GATTTCAAAA   1152

TAGTTGTAGC CTTATCCTGG TTTTACAGAT GTGAAACTTT CAAGAGATTT ACTGACTTTC   1212

CTAGAATAGT TTCTCTACTG GAAACCTGAT GCTTTTATAA GCCATTGTGA TTAGGATGAC   1272

TGTTACAGGC TTAGCTTTGT GTGAAAACCA GTCACCTTTC TCCTAGGTAA TGAGTAGTGC   1332
```

-continued

```
TGTTCATATT ACTTTAGTTC TATAGCATAC TGCATCTTTA ACATGCTATC ATAGTACATT      1392

TAGAATGATT GCCTTTGATT TTTTTTTTAA ATTCTGTGTG TGTGTGTGTA AAATGCCAAT      1452

TAAGAACACT GGTTTCATTC CATGTAAGCA TTAAACAGTG TATGTAGGTT TCAAGAGATT      1512

GTGATGATTC TTAAATTTTA ACTACCTTCA CTTAATATGC TTGAACTGTC GCCTTAACTA      1572

TGTTAAGCAT CTAGACTAAA AGCCAAAATA TAATTATTGC TGCCTTTCTA AAACCCAAA       1632

ATGTAGTTCT CTATTAACCT GAAATGTACA CTAGCCCAGA ACAGTTTAAT GGTACTTACT      1692

GAGCTATAGC ATAGCTGCTT AGTTGTTTTT GAGAGTTTTT AGTCAACACA TAATGGAAAC      1752

TTCTTTCTTC TAAAAGTTGC CAGTGCCACT TTTAAGAAGT GAATCACTAT ATGTGATGTA      1812

AAAGTTATTA CACTAAACAG GATAAACTTT TGACTCCCCT TTTGTTCATT TGTGGATTAA      1872

GTGGTATAAT ACTTAATTTT GGCATTTGAC TCTTAAGATT ATGTAACCTA GCTACTTTGG      1932

GATGGTCTTA GAATATTTTT CTGATAACTT GTTCCTTTTC CTGACTCCTC CTTGCAAACA      1992

AAATGATAGT TGACACTTTA TCCTGATTTT TTTCTTCTTT TTGGTTTATG TCTATTCTAA      2052

TTAAATATGT ATAAATAAAA AAAAAAAAAA AA                                    2084
```

(2) INFORMATION FOR SEQ ID NO: 2:

(i) SEQUENCE CHARACTERISTICS:
        (A) LENGTH: 298 amino acids
        (B) TYPE: amino acid
        (D) TOPOLOGY: linear (ii) MOLECULE TYPE: protein (xi) SEQUENCE DESCRIPTION: SEQ ID NO: 2:

```
Met Ser Leu Tyr Pro Ser Leu Glu Asp Leu Lys Val Asn Lys Leu Ile
 1               5                  10                  15

Gln Ala Gln Thr Ala Phe Ser Ala Asn Pro Ala Asn Pro Ala Ile Leu
             20                  25                  30

Ser Glu Ala Ser Ala Pro Ile Pro His Asp Gly Asn Leu Tyr Pro Arg
         35                  40                  45

Leu Tyr Pro Glu Leu Ser Gln Tyr Met Gly Leu Ser Leu Asn Glu Glu
     50                  55                  60

Glu Ile Arg Ala Asn Val Ala Val Ser Gly Ala Pro Leu Gln Gly
 65                  70                  75                  80

Gln Leu Val Ala Arg Pro Ser Ser Ile Asn Tyr Met Val Ala Pro Val
                 85                  90                  95

Thr Gly Asn Asp Val Gly Ile Arg Arg Ala Glu Ile Lys Gln Gly Ile
            100                 105                 110

Arg Glu Val Ile Leu Cys Lys Asp Gln Asp Gly Lys Ile Gly Leu Arg
        115                 120                 125

Leu Lys Ser Ile Asp Asn Gly Ile Phe Val Gln Leu Val Gln Ala Asn
    130                 135                 140

Ser Pro Ala Ser Leu Val Gly Leu Arg Phe Gly Asp Gln Val Leu Gln
145                 150                 155                 160

Ile Asn Gly Glu Asn Cys Ala Gly Trp Ser Ser Asp Lys Ala His Lys
                165                 170                 175

Val Leu Lys Gln Ala Phe Gly Glu Lys Ile Thr Met Thr Ile Arg Asp
            180                 185                 190

Arg Pro Phe Glu Arg Thr Ile Thr Met His Lys Asp Ser Thr Gly His
        195                 200                 205
```

-continued

```
Val Gly Phe Ile Phe Lys Asn Gly Lys Ile Thr Ser Ile Val Lys Asp
    210                 215                 220

Ser Ser Ala Ala Arg Asn Gly Leu Leu Thr Glu His Asn Ile Cys Glu
225                 230                 235                 240

Ile Asn Gly Gln Asn Val Ile Gly Leu Lys Asp Ser Gln Ile Ala Asp
                245                 250                 255

Ile Leu Ser Thr Ser Gly Thr Val Val Thr Ile Thr Ile Met Pro Ala
            260                 265                 270

Phe Ile Phe Glu His Ile Ile Lys Arg Met Ala Pro Ser Ile Met Lys
        275                 280                 285

Ser Leu Met Asp His Thr Ile Pro Glu Val
    290                 295
```

US 6,548,650 B1

NUCLEIC ACID ENCODING MELANOMA DIFFERENTIATION ASSOCIATED GENE-9

This application is a continuation of PCT International Application No. PCT/US97/24030, filed Dec. 30, 1997, designating the United States of America, which is a continuation-in-part of U.S. Ser. No. 08/774,465 now U.S. Pat. No. 6,071,696, filed Dec. 30, 1996, the contents of which are hereby incorporated by reference into the present application.

The invention disclosed herein was made with Government support under National Cancer Institute Grant No. CA35675. Accordingly, the U.S. Government has certain rights in this invention.

Throughout this application, various references are referred to within parentheses. Disclosures of these publications in their entireties are hereby incorporated by reference into this application to more fully describe the state of the art to which this invention pertains. Full bibliographic citation for these references may be found at the end of this application, preceding the claims.

BACKGROUND OF THE INVENTION

Terminal differentiation in human melanoma cells correlates with temporal changes in the expression of specific target genes. To define those genes that may be critical for this process a subtraction hybridization approach was used. cDNA libraries were constructed from actively proliferating HO-1 human melanoma cells (driver cDNA library) and cultures treated for various time periods with the combination of recombinant human fibroblast interferon (IFN-β) and mezerein (MEZ) (temporally spaced tester cDNA library) that induces terminal differentiation (Jiang and Fisher, 1993). From these two cDNA libraries, an HO-1 IFN-β+ MEZ temporally spaced subtracted (TSS) cDNA library was constructed. Random screening of this TSS cDNA library identifies cDNAs that display differential expression as a function of induction of growth arrest and terminal differentiation, called melanoma differentiation associated (mda) genes. In the present study the properties of the novel mda-9 gene were analyzed. This cDNA encodes a unique protein of 298 amino acids with a predicted size of 32 to ~34 kDa. Southern blotting analysis indicates that mda-9 is an evolutionary conserved gene. Tissue distribution analysis documents comparable expression in fifty human tissues, with slightly elevated expression in brain (putamen) and spleen (adult and fetal). Treatment of HO-1 human melanoma cells with IFN-β+MEZ results in a biphasic induction of mda-9 with maximum expression 8 and 12 h posttreatment and reduced expression at 24 h. In terminally differentiated and irreversibly growth arrested human melanoma cells, the level of mda-9 mRNA is reduced. The suppression in mda-9 expression is not simply a function of growth inhibition, since treatment of HO-1 cells with interferons, including IFN-β, leukocyte interferon (IFN-α) or immune interferon (IFN-γ), elevates mda-9 expression even though they suppress growth. These studies demonstrate that subtraction hybridization using temporally spaced RNA samples, resulting in a TSS cDNA library, can identify genes, such as mda-9, that are down-regulated during terminal cell differentiation in human melanoma cells. Further studies are necessary to define the precise role of mda-9 in the process of terminal differentiation.

Cancer is a progressive disease characterized by both qualitative and quantitative changes in the phenotypes of evolving tumor cells (1–5). Although cancer can develop as a consequence of single or multiple genetic alterations, a common theme in carcinogenesis involves abnormal programs of differentiation (6–10). Attempts to exploit this defective differentiation process in cancer cells has led to the development of a therapeutic approach called 'differentiation therapy' (6–11). This strategy is based on the use of single or multiple agents that induce cancer cells to become more differentiated with a concomitant reduction or loss of growth potential (6–12). In order to utilize differentiation therapy as an effective clinical tool, further research is necessary to identify agents capable of efficiently inducing terminal differentiation in cancer cells without inducing nonspecific toxicity in normal cells. Additionally, the identification of genes that correlate with and may mediate terminal cell differentiation would represent valuable reagents for defining the molecular basis of terminal cell differentiation, for direct cancer therapeutic applications and for screening compounds for potential use in differentiation therapy (6–12).

In cultured human melanoma cells, the combination of IFN-β+MEZ results in terminal cell differentiation and an irreversible loss of proliferative potential (11, 13, 14). In this model system, a single treatment for 24 h is sufficient to induce >95% terminal differentiation in cells subsequently grown for 72 h in the absence of inducers (14,15). The rapid induction of terminal differentiation in the vast majority of treated cancer cells makes this system amenable for defining those gene expression changes that occur during and that may mediate this process (11,12,16-19). To begin to address on a molecular level the question of growth control and terminal differentiation in human melanoma cells and to directly clone genes involved in these processes we developed and used an efficient subtraction hybridization protocol (16). This approach has resulted in the cloning of both known and novel cDNAs that are differentially regulated during growth suppression, reversible differentiation and terminal differentiation in human melanoma and other cancer cell types (16–20). The contents of U.S. Pat. No. 5,643,761, issued Jul. 1, 1997 to Fisher et al. entitled "Method for Generating a Subtracted cDNA Library and Uses of the Generated Library" and of International Application PCT/US94/12160 filed Oct. 24, 1994, entitled "Method for Generating a Subtracted cDNA Library and Uses of the Generated Library" which published May 4, 1995 as WO 95/11986 are hereby incorporated by reference.

In the present study, the properties of a novel mda-9 gene identified by subtraction hybridization were described. mda-9 is an evolutionary conserved gene that encodes a protein of ~32 to ~34 kDa without sequence homology to previously identified proteins. Expression of mda-9 is seen in fifty human tissues, with slightly elevated expression in brain (putamen) and spleen (adult and fetal). Induction of growth suppression and differentiation in human melanoma cells following exposure to IFN-β+MEZ results in a decrease in mda-9 expression. These studies provide additional support for the hypothesis that induction of terminal differentiation and irreversible growth arrest in human melanoma cells involves multiple gene expression changes, including increases as well as decreases in the expression of specific target genes.

SUMMARY OF THE INVENTION

This invention provides a method for producing a temporally spaced subtracted cDNA library comprising: a) isolating temporally spaced RNAs from cells; b) generating cDNA inserts from the RNAs isolated from step (a); c) producing a temporally spaced cDNA library having clones containing the cDNA inserts generated from step (b); d)

producing double stranded cDNA inserts from the temporally spaced cDNA library; e) denaturing the double stranded cDNA inserts; f) contacting the denatured double stranded cDNA inserts produced in step (e) with single-stranded DNAs from another cDNA library under conditions permitting hybridization of the single-stranded DNAs and the double-stranded cDNA inserts; g) separating the hybridized cDNA inserts from the unhybridized inserts; h) generating a cDNA library of the unhybridized inserts, thereby generating a temporally spaced subtracted cDNA library.

This invention further provides a temporally spaced subtracted library generated by the method for producing a temporally spaced subtracted cDNA library comprising: a) isolating temporally spaced RNAs from cells; b) generating cDNA inserts from the RNAs isolated from step (a); c) producing a temporally spaced cDNA library having clones containing the cDNA inserts generated from step (b); d) producing double stranded cDNA inserts from the temporally spaced cDNA library; e) denaturing the double stranded cDNA inserts; f) contacting the denatured double stranded cDNA inserts produced in step (e) with single-stranded DNAs from another cDNA library under conditions permitting hybridization of the single-stranded DNAs and the double-stranded cDNA inserts; g) separating the hybridized cDNA inserts from the unhybridized inserts; h) generating a cDNA library of the unhybridized inserts, thereby generating a temporally spaced subtracted cDNA library.

This invention provides a temporally spaced subtracted library generated by using HO-1 melanoma cells treated with IFN-β and MEZ in a temporally spaced manner at 2, 4, 8, 12, 24, and 48 hours and, wherein the single-stranded nucleic acid molecules are from another cDNA library of HO-1 melanoma cells.

This invention provides a method of identifying a melanoma differentiation associated gene comprising: a) generating probes from clones of the temporally spaced subtracted library generated by using HO-1 melanoma cells treated with IFN-β and MEZ in a temporally spaced manner at 2, 4, 8, 12, 24, and 48 hours and cells, wherein the single-stranded nucleic acid molecules are from another cDNA library of HO-1 melanoma cells; and b) hybridizing the probe with the total RNAs or mRNAs from HO-1 cells treated with IFN-β and MEZ and the total RNAs or mRNAs from untreated HO-1 cells, hybridization of the probe with the total RNAs or mRNAs from the treated HO-1 cell but altered [no, reduced, or enhanced] hybridization with the total RNAs or mRNA from untreated cells indicating that the clone from which the probe is generated carries a melanoma differentiation associated gene.

This invention provides a melanoma differentiation associated gene identified by the above described method of identifying a melanoma differentiation associated gene.

This invention provides a method of identifying temporally expressed genes from a single subtracted cDNA library, comprising: a) cloning the cDNAs from the temporally spaced subtracted cDNA library produced by the above described method for producing a temporally spaced subtracted cDNA library; b) hybridizing the clones obtained in step (a) with total RNAs isolated from control and with RNAs from differentiation-inducer treated cells, hybridization of the probe RNAs from differentiation-inducer treated cells, either enhanced or no or reduced hybridization with total RNA isolated from control cells indicating that the gene from which the probe was isolated is temporally expressed, thereby identifying temporally expressed genes from a single subtracted cDNA library.

This invention provides a temporally expressed gene identified by the above described method.

This invention provides an isolated mda-9 gene. This invention also provides an isolated nucleic acid having the nucleic acid sequence set forth in FIG. 7. This invention provides an isolated nucleic acid having the nucleic acid sequence set forth in FIG. 7, said nucleic acid encoding a human protein, wherein the encoded human protein is human mda-9. This invention also provides a human mda-9 protein having the amino acid sequence set forth in FIG. 7.

This invention provides a method for identifying a compound capable of inducing terminal differentiation in cancer cells comprising: a) incubating an appropriate concentration of the cancer cells with an appropriate concentration of the compound; b) measuring the expression of mda-9, the reduced expression of mda-9 gene indicating that the compound is capable of inducing terminal differentiation in cancer cells.

This invention provides a method for identifying a compound capable of inducing specific patterns of DNA damage caused by UV irradiation and gamma irradiation in human melanoma cells comprising: a) incubating an appropriate concentration of the human melanoma cells with an appropriate concentration of the compound; and b) measuring the expression of mda-9, the altered expression of mda-9 gene indicating that the compound is capable of inducing specific patterns of DNA damage caused by UV irradiation and gamma irradiation in human melanoma cells.

This invention provides a method for identifying a temporally expressed gene from cancer cells induced to undergo apoptosis by a chemotherapeutic agent, comprising: a) incubating an appropriate concentration of the cancer cells with an appropriate concentration of the chemotherapeutic agent; and b) measuring the expression of mda-9, the modified expression of mda-9 gene indicating that the compound is capable of inducing the cancer cells to undergo apoptosis.

This invention provides a method for identifying a compound capable of elevating mda-9 expression in cancer cells comprising: a) incubating an appropriate concentration of the cancer cells with an appropriate concentration of the compound; b) measuring the expression of mda-9 to determine whether the expression of the mda-9 gene is elevated.

This invention provides a method for detecting the presence of cytokines in a sample comprising a) contacting the sample with cancerous cells; b) measuring the expression of the mda-9 gene; c) determining whether the expression of the mda-9 gene is altered, the altered expression of the mda-9 gene in the cancerous cells indicating the presence of cytokines.

This invention provides an antisense oligonucleotide having a sequence capable of specifically hybridizing to an mRNA molecule encoding a human mda-9 protein so as to prevent expression of the mRNA molecule. This invention provides an antisense oligonucleotide having a sequence capable of specifically hybridizing to an mRNA molecule encoding a human mda-9 protein so as to prevent translation of the mRNA molecule.

This invention provides an antisense oligonucleotide having a sequence capable of specifically hybridizing to the promoter of the isolated nucleic acid molecule of an mda-9 gene, wherein the encoded mda-9 protein is a human protein, thereby preventing mRNA transcription.

This invention provides an antisense oligonucleotide having a sequence capable of specifically hybridizing to the mRNA of the isolated nucleic acid molecule of an mda-9 gene, wherein the encoded mda-9 protein is a human protein, and capable of degrading the hybridized mRNA.

This invention provides a purified mda-9 protein. This invention provides a purified human mda-9 protein. This invention further provides a purified human mda-9 protein having an amino acid sequence as set forth in FIG. 7.

This invention provides an antibody directed to a purified mda-9 protein. This invention provides an antibody directed to a purified human mda-9 protein. This invention further provides an antibody directed to a purified human mda-9 protein having an amino acid sequence as set forth in FIG. 7. This invention further provides an antibody capable of specifically recognizing an mda-9 protein. In an embodiment of the invention, the antibody is capable of specifically recognizing a human mda-9 protein.

This invention provides a pharmaceutical composition comprising an amount of the antisense oligonucleotide having a sequence capable of specifically hybridizing to an mRNA molecule encoding a human mda-9 protein so as to prevent expression of the mRNA molecule, to prevent translation of the mRNA molecule, effective to prevent expression of a human mda-9 protein and a pharmaceutically acceptable carrier. This invention also provides a pharmaceutical composition comprising an amount of the antisense oligonucleotide having a sequence capable of specifically hybridizing to the promoter of the isolated nucleic acid molecule of an mda-9 gene, wherein the encoded mda-9 protein is a human protein, thereby preventing mRNA transcription, effective to prevent expression of a human mda-9 protein and a pharmaceutically acceptable carrier. This invention further provides a pharmaceutical composition comprising an amount of the antisense oligonucleotide having a sequence capable of specifically hybridizing to the mRNA of the isolated nucleic acid molecule of an mda-9 gene, wherein the encoded mda-9 protein is a human protein and capable of degrading the hybridized mRNA, effective to prevent expression of a human mda-9 protein and a pharmaceutically acceptable carrier.

This invention provides a method of treating melanoma in a subject by administering a pharmaceutical composition comprising an amount of any one of the above described antisense oligonucleotides effective to prevent expression of a human mda-9 protein and a pharmaceutically acceptable carrier, thereby treating melanoma in a subject.

This invention provides a method of administering a pharmaceutical composition comprising an amount of any one of the above described antisense oligonucleotides effective to prevent expression of a human mda-9 protein and a pharmaceutically acceptable carrier.

This invention provides a method of inhibiting expression of a mda-9 gene in a subject comprising introducing a vector containing a nucleic acid molecule which renders the mda-9 gene functionless into the subject under conditions permitting the inhibition of the expression of the mda-9 gene.

This invention provides a method of treating a cancer in a subject by administering a pharmaceutical composition comprising an effective amount of the antibody capable of specifically recognizing an mda-9 protein, thereby treating the cancer in a subject.

This invention provides a method of increasing the expression of mda-9 to inhibit cell growth comprising transfecting cells with an expression vector comprising an mda-9 gene insert to induce expression of mda-9 in cells thereby inhibiting growth of the cells.

This invention also provides a method of treating a cancer in a subject by increasing mda-9 expression in cancer cells of the subject to induce partial differentiation in the cancer cells by administering a pharmaceutical composition comprising a targeting vector and an agent which partially induces differentiation.

This invention further provides a method of treating a cancer in a subject by increasing mda-9 expression in cancer cells of the subject to suppress growth of the cancer cells by administering a pharmaceutical composition comprising a targeting vector and an agent which partially induces differentiation.

This invention provides a cell having an exogenous indicator gene under the control of the regulatory element of a mda-9 gene.

This invention provides a nucleic acid molecule comprising a sequence of the promoter of an mda-9 gene protein.

BRIEF DESCRIPTION OF THE FIGURES

FIG. 7. Complete sequence of mda-9 (SEQ ID NO:1) Predicted translation of the mda-9 cDNA begins at nucleotide 76 and ends at nucleotide 972. Accession number AF006636 (Genbank). Mda-9 encodes a 298 amino acid protein with an $M_r$ of 32,480 (SEQ ID NO:2).

FIGS. 9A–9B. Temporal and dose kinetics of IFN-γ enhancement in mda-9 expression in HO-1 human melanoma cells. HO-1 cells were treated for the indicated time (FIG. 9A) and dose (FIG. 9B) of IFN-γ, RNA was then isolated and analyzed by Northern blotting. Results indicate the fold-change relative to control untreated cultures. Replicate samples varied by ≦15%.

DETAILED DESCRIPTION OF THE INVENTION

Figure 1:
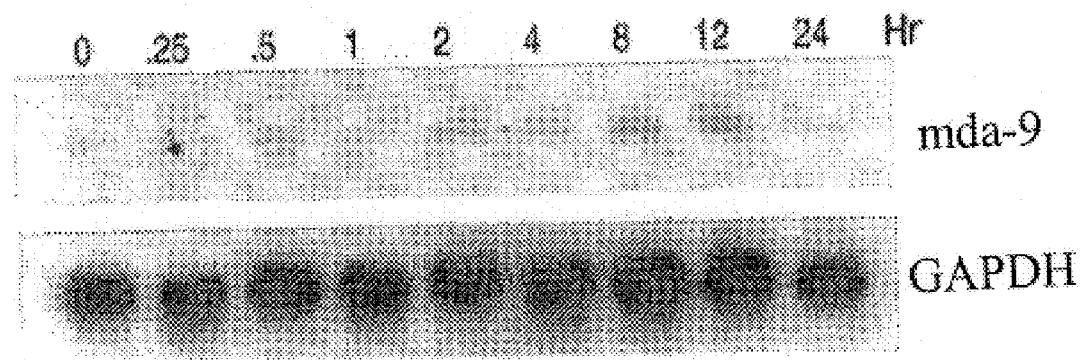
FIG. 1. Temporal expression of mda-9 in HO-1 cells exposed to IFN-β+MEZ. RNAs were isolated from untreated and HO-1 cells treated with IFN-β+MEZ(2000 U/ml+10 ng/ml) for 0.25, 0.5, 1, 2, 4, 8, 12 and 24 h. Ten micrograms of total cellular RNA were separated on 1% agarose gel, transferred to nylon membranes, sequentially hybridized with an mda-9 and then a GAPDH probe, and then exposed to autoradiography.

This invention provides a method for producing a temporally spaced subtracted cDNA library comprising: a) isolating temporally spaced RNAs from cells; b) generating cDNA inserts from the RNAs isolated from step (a); c) producing a temporally spaced cDNA library having clones containing the cDNA inserts generated from step (b); d) producing double stranded cDNA inserts from the temporally spaced cDNA library; e) denaturing the double stranded cDNA inserts; f) contacting the denatured double stranded cDNA inserts produced in step (e) with single-stranded DNAs from another cDNA library under conditions permitting hybridization of the single-stranded DNAs and the double-stranded cDNA inserts; g) separating the hybridized cDNA inserts from the unhybridized inserts; h) generating a cDNA library of the unhybridized inserts, thereby generating a temporally spaced Subtracted cDNA library.

As used herein "temporally spaced RNAs" are defined as RNAs collected over a sequential period of time. As used herein "temporally spaced subtracted cDNA library" is a cDNA library generated using a temporally spaced cDNA library having clones containing the cDNA inserts generated from temporally spaced RNAs to which single-stranded DNAs from another cDNA library are hybridized and separated, resulting in the "subtracted" unhybridized cDNA insert library.

In an embodiment of the invention, the cDNA library used to generate the single-stranded DNAs is from the same cell population as the cell population used to generate the temporally spaced cDNA library. In a further embodiment of the invention, the cDNA library allows propagation in single-stranded circle form. In a preferred embodiment of the invention, the cDNA library is a λZAP cDNA library.

In an embodiment of the invention, the double stranded cDNA inserts in step (d) are produced by releasing double-stranded cDNA inserts from double-stranded cDNA clones of the temporally spaced cDNA library with appropriate restriction enzymes. In another embodiment of the invention, the single-stranded cDNAs are labeled with biotin. In an embodiment of the invention, the separating of step f) is performed by extraction with streptavidin-phenol: chloroform. In a preferred embodiment of the invention, the cells are HO-1 human melanoma cells treated with IFN-β and MEZ. In a preferred embodiment of the invention, the treatment with IFN-β and MEZ is temporally spaced. In a further preferred embodiment of the invention, the temporally spaced treatment occurs at 2, 4, 8, 12, 24, and 48 hours.

In an embodiment of the invention, the single-stranded nucleic acid molecules are from another cDNA library of HO-1 melanoma cells. In a further embodiment of the invention, the cells are terminally differentiated and the single-stranded cDNAs are from another cDNA library of undifferentiated cells. In another embodiment of the invention, the cells are undifferentiated and the single-stranded cDNAs are from another cDNA library of terminally differentiated cells.

In a preferred embodiment of the invention, the cells are cancerous cells. In a further embodiment of the invention, the cancerous cells are selected from a group consisting of melanoma cells, basal cell carcinoma cells, squamous cell carcinoma cells, neuroblastoma cells, glioblastoma multiforme cells, myeloid leukemic cells, breast carcinoma cells, colon carcinoma cells, endometrial carcinoma cells, lung carcinoma cells, ovarian carcinoma cells, prostate carcinoma cells, cervical carcinoma cells, osteosarcoma cells and lymphoma cells.

In an embodiment of the invention, the cells are induced to undergo reversible growth arrest, DNA damage, or apoptosis and the single-stranded cDNAs are from another cDNA library of uninduced cells. In another embodiment of the invention, the cells are uninduced cells and the single-stranded cDNAs are from cells induced to undergo reversible growth arrest, DNA damage, or apoptosis.

As used herein, apoptosis is defined as programmed cell death.

In an embodiment of the invention, the cells are at one developmental stage and the single-stranded cDNAs are from another cDNA library of the cells at a different developmental stage. In another embodiment of the invention, the cells are cancerous and the single-stranded cDNAs are from another cDNA library from normal cells. In an embodiment of the invention, the cells are from the skin, connective tissue, muscle, breast, brain, meninges, spinal cord, colon, endometrium, lung, prostate and ovary.

This invention further provides a method further comprising introducing the subtracted library into host cells. In an embodiment of the invention, the method further comprises ligating the subtracted inserts into λ Uni-ZAP arms.

This invention further provides a temporally spaced subtracted library generated by the method for producing a temporally spaced subtracted cDNA library comprising: a) isolating temporally spaced RNAs from cells; b) generating cDNA inserts from the RNAs isolated from step (a); c) producing a temporally spaced cDNA library having clones containing the cDNA inserts generated from step (b); d) producing double stranded cDNA inserts from the temporally spaced cDNA library; e) denaturing the double stranded cDNA inserts; f) contacting the denatured double stranded cDNA inserts produced in step (e) with single-stranded DNAs from another cDNA library under conditions permitting hybridization of the single-stranded DNAs and the double-stranded cDNA inserts; g) separating the hybridized cDNA inserts from the unhybridized inserts; h) generating a cDNA library of the unhybridized inserts, thereby generating a temporally spaced subtracted cDNA library.

This invention provides a temporally spaced subtracted library generated by using HO-1 melanoma cells treated with IFN-β and MEZ in a temporally spaced manner at 2, 4, 8, 12, 24, and 48 hours and, wherein the single-stranded nucleic acid molecules are from another cDNA library of HO-1 melanoma cells.

This invention provides a method of identifying a melanoma differentiation associated gene comprising: a) generating probes from clones of the temporally spaced subtracted library generated by using HO-1 melanoma cells treated with IFN-β and MEZ in a temporally spaced manner at 2, 4, 8, 12, 24, and 48 hours and cells, wherein the single-stranded nucleic acid molecules are from another cDNA library of HO-1 melanoma cells; and b) hybridizing the probe with the total RNAs or mRNAs from HO-1 cells treated with IFN-β and MEZ and the total RNAs or mRNAs from untreated HO-1 cells, hybridization of the p robe with the total RNAs or mRNAs from the treated HO-1 cell but altered [no, reduced, or enhanced] hybridization with the total RNAs or mRNA from untreated cells indicating that the clone from which the probe is generated carries a melanoma differentiation associated gene. In an embodiment of the invention, the mRNAs are probed with labeled cDNA clones generated from the temporally spaced subtracted library on a dot blot, hybridization of the probe with the mRNAs isolating a melanoma differentiation associated gene.

This invention provides a melanoma differentiation associated gene identified by the above described method of identifying a melanoma differentiation associated gene.

This invention provides a method of identifying temporally expressed genes from a single subtracted cDNA library, comprising: a) cloning the cDNAs from the temporally spaced subtracted cDNA library produced by the above described method for producing a temporally spaced subtracted cDNA library; b) hybridizing the clones obtained in step (a) with total RNAs isolated from control and with RNAs from differentiation-inducer treated cells, hybridization of the probe RNAs from differentiation-inducer treated cells, either enhanced or no or reduced hybridization with total RNA isolated from control cells indicating that the gene from which the probe was isolated is temporally expressed, thereby identifying temporally expressed genes from a single subtracted cDNA library.

This invention provides a temporally expressed gene identified by the above described method. In an embodiment of the invention, the temporally expressed gene is cloned into a λ ZAP phage vector.

This invention provides an isolated mda-9 gene. In an embodiment of the invention, the isolated mda-9 gene is an isolated nucleic acid, wherein the encoded mda-9 protein is a human protein. This invention also provides an isolated nucleic acid having the nucleic acid sequence set forth in FIG. 7. This invention provides an isolated nucleic acid having the nucleic acid sequence set forth in FIG. 7, said nucleic acid encoding a human protein, wherein the encoded human protein is human mda-9. This invention also provides a human mda-9 protein having the amino acid sequence set forth in FIG. 7.

This invention provides a method for identifying a compound capable of inducing terminal differentiation in cancer cells comprising: a) incubating an appropriate concentration of the cancer cells with an appropriate concentration of the compound; b) measuring the expression of mda-9, the reduced expression of mda-9 gene indicating that the compound is capable of inducing terminal differentiation in cancer cells. In an embodiment of the invention, the cancer cells are selected from a group consisting of melanoma cells, basal cell carcinoma cells, squamous cell carcinoma cells, neuroblastoma cells, glioblastoma multiforme cells, myeloid leukemic cells, breast carcinoma cells, colon carcinoma cells, endometrial carcinoma cells, lung carcinoma cells, ovarian carcinoma cells, prostate carcinoma cells, cervical carcinoma cells, osteosarcoma cells and lymphoma cells.

This invention provides a method for identifying a compound capable of inducing specific patterns of DNA damage caused by UV irradiation and gamma irradiation in human melanoma cells comprising: a) incubating an appropriate concentration of the human melanoma cells with an appropriate concentration of the compound; and b) measuring the expression of mda-9, the altered expression of mda-9 gene indicating that the compound is capable of inducing specific patterns of DNA damage caused by UV irradiation and gamma irradiation in human melanoma cells.

This invention provides a method for identifying a temporally expressed gene from cancer cells induced to undergo apoptosis by a chemotherapeutic agent, comprising: a) incubating an appropriate concentration of the cancer cells with an appropriate concentration of the chemotherapeutic agent; and b) measuring the expression of mda-9, the modified expression of mda-9 gene indicating that the compound is capable of inducing the cancer cells to undergo apoptosis. In an embodiment of the invention, the cancer cells are selected from a group consisting of melanoma cells, basal cell carcinoma cells, squamous cell carcinoma cells, neuroblastoma cells, glioblastoma multiforme cells, myeloid leukemic cells, breast carcinoma cells, colon carcinoma cells, endometrial carcinoma cells, lung carcinoma cells, ovarian carcinoma cells, prostate carcinoma cells, cervical carcinoma cells, osteosarcoma cells and lymphoma cells.

This invention provides a method for identifying a compound capable of elevating mda-9 expression in cancer cells comprising: a) incubating an appropriate concentration of the cancer cells with an appropriate concentration of the compound; b) measuring the expression of mda-9 to determine whether the expression of the mda-9 gene is elevated. In an embodiment of the invention, the compound capable of elevating mda-9 expression in cancer cells is IFN-γ. In another embodiment of the invention, the compound capable of elevating mda-9 expression in cancer cells is a cytokine. In a further embodiment of the invention, the cytokine is selected from a group consisting of IFN-α, IFN-β, IFN-γ, TNF-α, stem cell growth factors, colony stimulating factor, GMCSF, and interleukins [including interleukin-6]. In a still further embodiment of the invention, the cancer cells are selected from a group consisting of human melanoma cells, basal cell carcinoma cells, squamous cell carcinoma cells, neuroblastoma cells, glioblastoma multiforme cells, myeloid leukemic cells, breast carcinoma cells, colon carcinoma cells, endometrial carcinoma cells, lung carcinoma cells, ovarian carcinoma cells, prostate carcinoma cells, cervical carcinoma cells, osteosarcoma cells and lymphoma cells.

This invention provides a method for detecting the presence of cytokines in a sample comprising a) contacting the sample with cancerous cells; b) measuring the expression of the mda-9 gene; c) determining whether the expression of the mda-9 gene is altered, the altered expression of the mda-9 gene in the cancerous cells indicating the presence of cytokines.

This invention provides an antisense oligonucleotide having a sequence capable of specifically hybridizing to an mRNA molecule encoding a human mda-9 protein so as to prevent expression of the mRNA molecule. This invention provides an antisense oligonucleotide having a sequence capable of specifically hybridizing to an mRNA molecule encoding a human mda-9 protein so as to prevent translation of the mRNA molecule.

This invention provides an antisense oligonucleotide having a sequence capable of specifically hybridizing to the promoter of the isolated nucleic acid molecule of an mda-9 gene, wherein the encoded mda-9 protein is a human protein, thereby preventing mRNA transcription.

This invention provides an antisense oligonucleotide having a sequence capable of specifically hybridizing to the mRNA of the isolated nucleic acid molecule of an mda-9 gene, wherein the encoded mda-9 protein is a human protein, and capable of degrading the hybridized mRNA.

This invention provides a purified mda-9 protein. This invention also provides a purified human mda-9 protein. This invention further provides a purified human mda-9 protein having an amino acid sequence as set forth in FIG. 7.

This invention provides an antibody directed to a purified mda-9 protein. This invention provides an antibody directed to a purified human mda-9 protein. This invention further provides an antibody directed to a purified human mda-9 protein having an amino acid sequence as set forth in FIG. 7. This invention further provides an antibody capable of specifically recognizing an mda-9 protein. In an embodiment of the invention, the antibody is capable of specifically recognizing a human mda-9 protein. In an embodiment the antibody is capable of specifically recognizing a human mda-9 protein having an amino acid sequence as set forth in FIG. 7. In an embodiment of the invention, the antibody is a monoclonal or polyclonal antibody directed to a purified mda-9 protein. In another embodiment of the invention, the antibody is a monoclonal or polyclonal antibody capable of specifically recognizing an mda-9 protein. In another embodiment of the invention, the antibody is a monoclonal or polyclonal antibody capable of specifically recognizing a human mda-9 protein. In another embodiment of the invention, the antibody is a monoclonal or polyclonal antibody capable of specifically recognizing a human mda-9 protein having an amino acid sequence as set forth in FIG. 7. The above-described antibody is also useful for the detection of mda-9 protein.

This invention provides a pharmaceutical composition comprising an amount of the antisense oligonucleotide having a sequence capable of specifically hybridizing to an mRNA molecule encoding a human mda-9 protein so as to prevent expression of the mRNA molecule, to prevent translation of the mRNA molecule, effective to prevent expression of a human mda-9 protein and a pharmaceutically acceptable carrier. This invention also provides a pharmaceutical composition comprising an amount of the antisense oligonucleotide having a sequence capable of specifically hybridizing to the promoter of the isolated nucleic acid molecule of an mda-9 gene, wherein the encoded mda-9 protein is a human protein, thereby preventing mRNA transcription, effective to prevent expression of a human mda-9 protein and a pharmaceutically acceptable carrier. This invention further provides a pharmaceutical composition comprising an amount of the antisense oligonucleotide having a sequence capable of specifically hybridizing to the mRNA of the isolated nucleic acid molecule of an mda-9 gene, wherein the encoded mda-9 protein is a human protein and capable of degrading the hybridized mRNA, effective to prevent expression of a human mda-9 protein and a pharmaceutically acceptable carrier.

This invention provides a method of treating cancer in a subject by administering the above described pharmaceutical composition comprising an amount of any one of the above described antisense oligonucleotides effective to prevent expression of a human mda-9 protein and a pharmaceutically acceptable carrier, thereby treating melanoma in a subject. In an embodiment, the cancer is selected from a group consisting of human melanoma, basal cell carcinoma, squamous cell carcinoma, neuroblastoma, glioblastoma multiforme carcinoma, myeloid leukemia, breast carcinoma, colon carcinoma, endometrial carcinoma, lung carcinoma, ovarian carcinoma, prostate carcinoma, cervical carcinoma, osteosarcoma and lymphoma.

In an embodiment of the subject invention, the expression of a human mda-9 gene or protein is prevented by hybridization of an antisense oligonucleotide which is operatively linked to a tissue specific promoter which is capable of directing the expression of the antisense oligonucleotide in the specific cancer cells. As used herein, "operatively linked" shall mean that the expression of the antisense oligonucleotide is controlled by the tissue specific promoter. In another embodiment, the expression of a human mda-9 protein is prevented by hybridization of the antisense oligonucleotide to the mda-9 gene promoter or mda-9 mRNA molecules regulated by a tissue specific promoter that permits expression of the human mda-9 antisense sequence only in melanocyte and melanoma cells. In a further embodiment, the cancer is melanoma and the tissue specific promoter is a tyrosinase promoter.

This invention provides a method of administering a pharmaceutical composition comprising an amount of any one of the above described antisense oligonucleotides effective to prevent expression of a human mda-9 protein and a pharmaceutically acceptable carrier. In an embodiment of the invention, pharmaceutical composition further comprises a substance which facilitates the delivery of said oligonucleotide into the cell. As used herein, the substance which facilitates the delivery of the oligonucleotide into the cell may be a liposome or an antibody. In an embodiment of the invention, the oligonucleotide is introduced into the cell by a viral vector. In an embodiment of the invention, the oligonucleotide is stabilized, so as not to be degraded. This invention provides a method of inhibiting expression of a mda-9 gene in a subject comprising introducing a vector containing a nucleic acid molecule which renders the mda-9 gene functionless into the subject under conditions permitting the inhibition of the expression of the mda-9 gene.

As used herein, "functionless" is defined as inability of the mda-9 gene to encode the mda-9 protein, including inability to transcribe the mda-9 gene, or inability to translate the mda-9 protein.

In an embodiment of the invention, the nucleic acid is an antisense oligonucleotide having a sequence capable of specifically hybridizing to an mRNA molecule encoding a human mda-9 protein. In another embodiment of the invention, the nucleic acid contains a mutation or deletion of the mda-9 gene having the appropriate flanking sequences.

As used herein, the appropriate flanking sequences are defined as the sequences required in order for recombination to occur.

This invention provides a method of treating a cancer in a subject by administering a pharmaceutical composition comprising an effective amount of the antibody capable of specifically recognizing an mda-9 protein, thereby treating the cancer in a subject. In an embodiment of the invention, the cancer is a melanoma.

This invention provides a method of increasing the expression of mda-9 to inhibit cell growth comprising transfecting cells with an expression vector comprising an mda-9 gene insert to induce expression of mda-9 in cells thereby inhibiting growth of the cells. In an embodiment of the invention, the mda-9 gene insert is in either the sense or antisense orientation. In another embodiment of the invention, the mda-9 gene insert is in the sense orientation and mda-9 is overexpressed. In an embodiment of the invention, the mda-9 gene insert is in the antisense orientation and mda-9 expression is inhibited. In another embodiment the cells are selected from the group consisting of human melanoma, basal cell carcinoma, squamous cell carcinoma, neuroblastoma, glioblastoma multiforme carcinoma, myeloid leukemia, breast carcinoma, colon carcinoma, endometrial carcinoma, lung carcinoma, ovarian carcinoma, prostate carcinoma, cervical carcinoma, osteosarcoma and lymphoma.

This invention provides a method of treating a cancer in a subject by increasing mda-9 expression in cancer cells of the subject to induce partial differentiation in the cancer cells by administering a pharmaceutical composition comprising a targeting vector and an agent which partially induces differentiation. In an embodiment of the invention, the targeting vector is an mda-9 expression vector and said vector is selected from the group consisting of an adenovirus, an adeno-associated virus, a retrovirus, a vaccinia virus, and an Epstein Barr virus. In another embodiment of the invention, the agent which partially induces differentiation is a cytokine, a DNA damaging chemotherapeutic agent, or a physical therapeutic agent. In an embodiment of the invention, the cytokine is selected from the group consisting of IFN-α, IFN-β, IFN-γ and TNF-α. In another embodiment of the invention, the DNA damaging chemotherapeutic agent is selected from the group consisting of dactinomycin, cis-platinum, and taxol and its analogs. In an embodiment of the invention, the physical therapeutic agent is gamma irradiation. In an embodiment of the invention, the cancer cells are selected from the group consisting of human melanoma, basal cell carcinoma, squamous cell carcinoma, neuroblastoma, glioblastoma multiforme carcinoma, myeloid leukemia, breast carcinoma, colon carcinoma, endometrial carcinoma, lung carcinoma, ovarian carcinoma, prostate carcinoma, cervical carcinoma, osteosarcoma and lymphoma.

This invention provides a method of treating a cancer in a subject by increasing mda-9 expression in cancer cells of the subject to suppress growth of the cancer cells by administering a pharmaceutical composition comprising a targeting vector and an agent which partially induces differentiation. In an embodiment of the invention, the targeting vector is an mda-9 expression vector and said vector is selected from the group consisting of an adenovirus, an adeno-associated virus, a retrovirus, a vaccinia virus, and an Epstein Barr virus. In another embodiment of the invention, the agent which partially induces differentiation is a cytokine, a DNA damaging chemotherapeutic agent, or a physical therapeutic agent. In an embodiment of the invention, the cytokine is selected from the group consisting of IFN-α, IFN-β, IFN-γ and TNF-α. In another embodiment of the invention, the DNA damaging chemotherapeutic agent is selected from the group consisting of dactinomycin, cis-platinum, and taxol and its analogs. In an embodiment of the invention, the physical therapeutic agent is gamma irradiation. In an embodiment of the invention, the cancer cells are selected from the group consisting of human melanoma, basal cell carcinoma, squamous cell carcinoma, neuroblastoma, glioblastoma multiforme carcinoma, myeloid leukemia, breast carcinoma, colon carcinoma, endometrial carcinoma, lung carcinoma, ovarian carcinoma, prostate carcinoma, cervical carcinoma, osteosarcoma and lymphoma.

This invention provides a cell having an exogenous indicator gene under the control of the regulatory element of a mda-9 gene. In an embodiment of the invention, the cell is a normal cell. In another embodiment of the invention, the cell is a cancer cell. In any of the above-described embodiments of a cell having an exogenous indicator gene under the control of the regulatory element of a mda-9 gene, the indicator gene may code for beta-galactosidase, luciferase, chloramphenicol transferase or secreted alkaline phosphatase.

This invention provides a method for determining whether an agent is capable of modifying DNA damage and repair pathways, differentiation, apoptosis or operates through a cytokine modulatory pathway comprising contacting an amount of the agent with the cell of claim 88, wherein a change in expression of the indicator gene compared to the expression in control cells indicates that the agent modifies DNA damage and repair pathways, differentiation, apoptosis or operates through a cytokine modulatory pathway. The ability of an agent to modify DNA damage, modify DNA repair pathways, modify cell differentiation, modify apoptosis or to operate through a cytokine modulatory pathway may be mutually exclusive or an agent may also be capable of more than one type of activity or modification. In an embodiment of the invention, the change in expression is either a decrease in expression or an increase in expression of the indicator gene.

One of skill in the art will select appropriate control cells for the screening methods depending upon the desired "end point" characteristics sought for the screened molecules or agents. Control cells may be selected from, but not limited to, cells treated with a solvent rather than the molecule or the agent performing the above-described modifications, an agent which does not induce DNA damage, or a reporter-promoter construct driven by a constitutive promoter such as a CMV (cytomegalovirus) promoter. A desired small molecule or agent characteristic e.g. "end point" which is selected for by the screening method may be selected from, but not limited to, a change in cellular morphology, growth suppression of cells, upregulation of mda-9 or modification of any specific gene.

This invention provides a nucleic acid molecule comprising a sequence of the promoter of an mda-9 gene protein.

This invention provides a method to screen for either a small molecule or agent which modifies DNA damage and repair pathways, differentiation, or apoptosis, or operates through a cytokine modulatory pathway comprising: a) contacting an amount of the small molecule or agent with cells of claim 88; b) determining expression of the indicator gene; c) comparing the expression determined in step (b) with control cells, a modified expression of the indicator gene in the cells of step (a) compared to the control cells indicating that the small molecule or agent modifies DNA damage and repair pathways, differentiation, apoptosis or operates through a cytokine modulatory pathway.

In an embodiment of the invention, the modification in expression is either a decrease in expression or an increase in expression of the indicator gene. In another embodiment of the invention, the small molecule which alters the expression of the mda-9 gene or DNA-damaging agent is selected from a recombinatorial library, a peptide library, a peptide-derived library or a chemical library or a combinatorial chemical library. "Chemical libraries" have been defined as "intentionally created collections of differing molecules which can be prepared synthetically or biosynthetically". A type of synthetic strategy which can lead to large chemical libraries is "combinatorial chemistry". "Combinatorial chemistry" has been defined as "the systematic and repetitive, covalent connection of a set of different 'building blocks' of varying structures to each other to yield a large array of diverse molecular entities." (Gallop, M. A. et al. (1994) J. of Med. Chem. 37(9) 1233–1251.) Building blocks can include nucleotides, carbohydrates, peptides or peptoids into ordered structures. Chemical libraries generated utilizing combinatorial chemistry can display remarkable diversity. Peptide libraries may be selected from peptides or peptide mimics. The contents of WO 95/20591 (Stolowitz, M.) Aug. 3, 1995; WO/96/04403 (Burke, D. et al.) Feb. 15, 1996; WO 96/09316 (Eaton and Gold) Mar. 28, 1996; WO 96/27605(Gold, L. et al.) Sep. 12, 1996 which disclose inter alia production of chemical libraries, combinatorial libraries, and nucleotide libraries, are hereby incorporated by reference.

This invention provides an agent which is a small molecule selected from a recombinatorial library, a peptide library, a peptide-derived library or a chemical library. One of skill in the art will know which type of library is required for the screening method depending upon the desired characteristics of molecules to be screened for. Recombinatorial libraries may be chemically synthesized, e.g. a change in one atom of a chemical compound would create numerous "unknown" chemicals to be screened for a desired characteristic. The screening method would enable one of skill in the art to screen for small molecules or agents having the same properties or characteristics as an entire molecule, e.g. a small molecule with properties of a wholw molecule, e.g. having properties of a cytokine. The above described screening methods, e.g. using a reporter-promoter construct as a control, would enable one of skill in the art to find therapeutic agents which alter specific genes.

This invention will be better understood from the Experimental Details which follow. However, one skilled in the art will readily appreciate that the specific methods and results discussed are merely illustrative of the invention as described more fully in the claims which follow thereafter.

FIRST SERIES OF EXPERIMENTS

Experimental Details

Cell Lines and Culture Conditions. HO-1 is a melanotic melanoma cell line produced from a metastatic inguinal lymph node lesion from a 49 year-old female and was used between passages 150 and 175 (13,21,22). FM516-SV is a normal human melanocyte culture immortalized by the SV40 T-antigen gene (23). Additional melanoma cell lines established from patients with metastatic melanomas that were evaluated, include LO-1, SH-1, WM239, MeWo, SKMEL-p53 wt (containing a wild-type p53 gene) and SKMEL-p53 mut (containing a mutant p53 gene) (13,21, 24). Cultures were grown at 37° C. In a 95% air 5% $CO_2$-humidified incubator in Dulbecco's modified Eagle's medium (DMEM) supplemented with 5 or 10% fetal bovine serum (Hyclone, UT). Cultures were maintained in the logarithmic phase of growth by subculturing (1:5 or 1:10) prior to confluence approximately every 4 to 7 d. For determining steady-state RNA expression, cultures were seeded at $1.5 \times 10^6$ cells per 10-cm tissue culture plate, and 24 h later the medium was changed without inducers or with IFN-β (2000 U/ml), MEZ (10 ng/ml) or IFN-β+MEZ (2000 U/ml+10 ng/ml). Total cytoplasmic RNA was isolated at various time points and analyzed for mda-9 and GAPDH expression.

Cloning of mda-9 by Subtraction Hybridization. Identification and cloning of mda-9 was accomplished as described previously (16). Briefly, a cDNA library was prepared from RNA isolated from actively growing HO-1 cells (driver) and RNAs isolated from HO-1 cells treated with IFN-β+MEZ (2000 U/ml+10 ng/ml) for 2, 4, 8, 12 and 24 h (temporally spaced tester). Subtraction hybridization was then performed between double-stranded tester DNA and single-stranded driver DNA prepared by mass excision of the libraries. The TSS cDNAs were efficiently cloned into the λ Uni-ZAP phage vector and used to screen Northern blots containing total RNA isolated from control HO-1 cells and HO-1 cultures treated for 24 h with IFN-β (2000 U/ml), MEZ (10 ng/ml) or IFN-β+MEZ (2000 U/ml+10 ng/ml). This strategy resulted in the identification of a partial mda-9 cDNA (11). A full-length mda-9 cDNA was isolated following screening of a differentiation inducer-treated HO-1 cDNA library (16) and using the procedure of rapid amplification of cDNA ends (RACE) as described previously (17,25–27). Sequence analysis was determined as described (28,29).

RNA Isolation, Northern Blotting and Southern Blotting of Genomic DNAs. Total cellular RNA was isolated by the guanidinium/phenol procedure and Northern blotting was performed as described (30–32). Ten μg of RNA were denatured with glyoxal/dimethyl sulfoxide (DMSO), electrophoresed on 1.0% agarose gels, transferred to nylon membranes and hybridized to a $^{32}P$-labeled mda-9 probe and then after stripping the membranes were hybridized to a $^{32}p$-labeled rat GAPDH probe (33) as described previously (30–32). Following hybridization, the filters were washed and exposed for autoradiography. RNA blots were quantitated by densitometric analysis using a Molecular Dynamics densitometer (Sunnyvale, Calif.) (34). To determine human tissue specific expression of mda-9 a Human RNA Master Blot™ (Clontech Laboratories, Inc., Palo Alto, Calif.), containing poly $A^+$ RNA from 50 tissues immobilized as separate dots on a charged nylon membrane, was probed with a $^{32}P$-labeled mda-9 cDNA probe and following stripping the membrane was probed with a $^{32}P$-labeled human ubiquitin housekeeping cDNA probe as described by Clontech Laboratories, Inc. Following hybridization, the filters were washed and exposed for autoradiography.

Genomic DNAs for *Saccharomyces cerevisiae* (yeast), cat, dog, Rhesus monkey and normal human were obtained commercially (Promega Corp., Madison, Wis. and Clontech Laboratories Inc., Palo Alto, Calif.). Human DNA was also prepared from HeLa human cervical carcinoma cells. The DNAs were digested completely with HindIII restriction enzyme, electrophoresed, transferred to nylon membranes and hybridized to a $^{32}P$-labeled mda-9 gene probe (16,18, 32). After hybridization the nylon membranes were washed in 3×SSC, 0.1% SDS, 30 min; 1×SSC, 0.1% SDS, 30 min; and 0.1×SSC, 0.1% SDS, 20 min at 55° C.; and then exposed to autoradiography (18).

Reagents. Recombinant human IFN-β, with a serine substituted for a cysteine at position 17 of the molecule (35), was provided by Triton Bioscience (Alameda, Calif.). IFN-β was obtained as a lyophilized powder with a concentration of $4.5 \times 10^7$ U/ml. Recombinant human IFN-α (IFN-αA) was provided by Hoffmann-La Roche, Inc., N.J. Recombinant human IFN-γ was kindly provided by Dr. Sidney Pestka (UMDNJ-Robert Wood Johnson Medical School, N.J). The interferon titer of IFN-αA and IFN-β was determined using a cytopathic effect inhibition assay with vesicular stomatitis virus (VSV) on a bovine kidney cell line (MDBK) or human fibroblast AG-1732 cells (36). The interferon titer of IFN-γ was determined using a cytopathic effect inhibition assay with VSV on the human WISH cell line (36). The concentrated stocks of interferons were diluted to $1 \times 10^6$ U/ml in DMEM-10, frozen at −80° C., thawed immediately prior to use, and diluted to the appropriate concentration in DMEM-10. Stock solutions were maintained at 4° C. MEZ was obtained from Sigma Scientific Co. (St. Louis, Mo.). Stock solutions were prepared in DMSO, aliquoted into small portions, and stored at −20° C. The final concentration of DMSO did not alter growth or induce markers of differentiation (elevated melanin synthesis) in the cell lines used in the present study.

Experimental Results mda-9 Is Variably Expressed in HO-1 Cells Treated with IFN-β+MEZ. The subtraction hybridization strategy employed to identify genes involved in terminal cell differentiation has a high probability of detecting genes that display elevated expression in IFN-β+MEZ treated versus actively proliferating control HO-1 human melanoma cells (11). However, since cDNA libraries were constructed from pooled RNA samples obtained from HO-1 cells treated for various times with IFN-β+MEZ, i.e., 2, 4, 8, 12 and 24 h, it is equally possible that genes displaying biphasic patterns of gene expression can also be isolated from this TSS cDNA library. This is indeed the case as found with mda-9 which displays maximum enhanced expression 8 and 12 h after treatment with IFN-β+MEZ, whereas expression is lower than controls after 1 or 24 h treatment (FIG. 1). Exposure to IFN-β+MEZ for 2 or 4 h also elevates mda-9 expression, but to a lesser extent than after 8 or 12 h. On the basis of this study, if subtracted cDNA libraries had been produced solely from HO-1 cells treated for 24 h with IFN-β+MEZ the probability of isolating mda-9 cDNA clones would be significantly reduced. In this context, the temporally spaced subtracted (TSS) IFN-β+MEZ cDNA library should permit the cloning of additional genes that only display elevated expression in human melanoma cells during specific times within the first 24 h of treatment with IFN-β+MEZ.

mda-9 Is Down-Regulated in Terminally Differentiated Human Melanoma Cells. Treatment of human melanoma cells with IFN-β+MEZ (2000 U/ml+10 ng/ml) for 96 h results in growth suppression and terminal cell differentiation in the majority of treated cells (13,14,17). When grown in the single agent, growth suppression is less and the degree of inhibition depends on the specific melanoma analyzed (Table 1). Moreover, cultures treated with a single agent are not terminally differentiated (data not shown). The combination of agents either synergistically or additively reduces growth, depending on the melanoma cell line studied. Growth suppression induced by the combination of agents in specific melanomas is independent of the in vitro growth rate of these cells. For example, a >90% inhibition in growth is seen following 96 h treatment with IFN-β+MEZ in slow growing human melanomas, such as LO-1 and SKMEL-p53 wt, as well as rapidly growing human melanomas, such as HO-1 and WM239. Maximum growth suppression, >95% in comparison with untreated control cultures, is apparent in human melanoma cells, HO-1, LO-1 and SKMEL-p53 wt, encoding a wild-type p53 protein (Table 1). Two human melanoma cells with a previously defined mutation in p53, MeWo and SKMEL-p53 mut, display <75% reduction in growth when treated with IFN-β+MEZ. In contrast, WM239, with an immunologically mut p53 protein, displays a different profile of sensitivity than the other melanoma cells. WM239 cells treated with IFN-β+MEZ are inhibited by ~91% when grown in the combination of agents (Table 1). Growth of the SV40-immortalized human melanocyte cell line, FM516-SV, in IFN-β+MEZ results in an ~70% reduction in growth without inducing terminal differentiation in the majority of treated cells (17) (Table 1 and data not shown).

Figure 2:
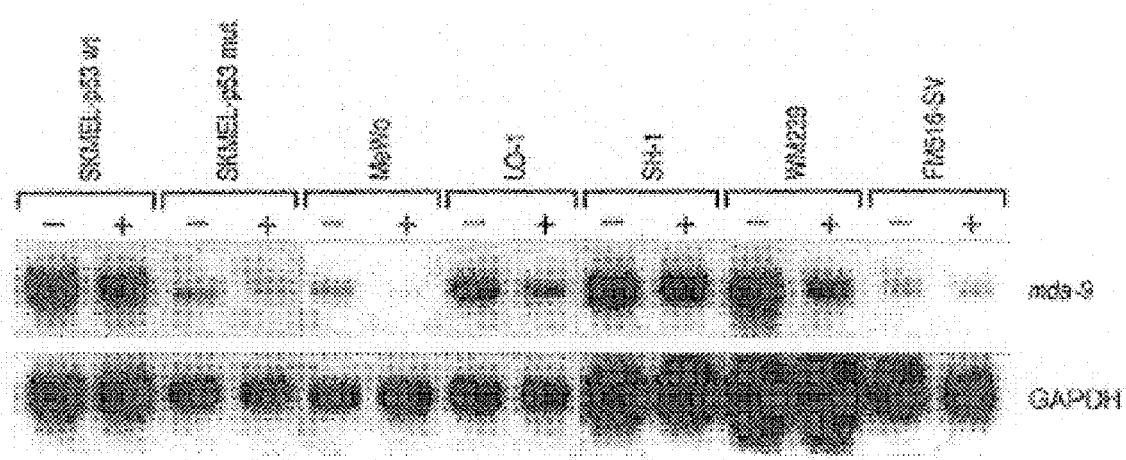
FIG. 2. Effects of IFN-β+MEZ on mda-9 expression in human melanoma cells and an SV40-immortalized human melanocyte cell line. The indicated cell line was grown in the presence or absence of IFN-β+MEZ (2000 U/ml+10 ng/ml) for 96 h and RNA was analyzed as described in FIG. 1.

To determine if induction of differentiation modifies mda-9 expression, RNAs were isolated from human melanoma and FM516-SV cells grown for 96 hr in the absence or presence of IFN-β+MEZ (2000 U/ml+10 ng/ml) (FIG. 2). In all of the cell lines, the combination of IFN-β+MEZ decreases the steady-state level of mda-9 RNA. Based on densitometer comparisons of mda-9 and GAPDH RNA levels, mda-9 RNA expression is reduced from ~1.5- to ~14-fold in treated cultures, with MeWo cells showing the greatest change and FM516-SV cells displaying the smallest change. A direct relationship between the level of reduction in mda-9 expression and the degree of growth suppression induced by IFN-β+MEZ is not apparent in the melanoma cell lines used in the present study.

TABLE 1

Effect of IFN-β and MEZ, alone and in combination, on the growth of human human melanoma and melanocyte cell lines Experimental Conditions[a]

| Cell Line | Control | IFN-β | | MEZ | | IFN-β + MEZ | |
|---|---|---|---|---|---|---|---|
| HO-1 | 64.5 ± 5.3 | 14.0 ± 2.6 | (22) | 16.8 ± 1.0 | (26) | 0.7 ± 0.2 | (1) |
| LO-1 | 17.0 ± 2.0 | 1.3 ± 0.3 | (8) | 4.7 ± 0.4 | (28) | 0.4 ± 0.1 | (2) |
| MeWo | 33.6 ± 1.2 | 15.6 ± 1.9 | (46) | 15.4 ± 1.9 | (46) | 9.4 ± 1.1 | (28) |
| SH-1 | 24.9 ± 1.6 | 14.3 ± 1.5 | (57) | 14.1 ± 0.3 | (57) | 8.0 ± 1.2 | (32) |
| SKMEL-p53 mut | 36.1 ± 4.8 | 39.5 ± 7.5 | (109) | 21.5 ± 4.3 | (60) | 9.3 ± 0.6 | (26) |
| SKMEL-p53 wt | 16.8 ± 0.8 | 9.1 ± 0.3 | (54) | 3.6 ± 0.7 | (21) | 0.7 ± 0.2 | (4) |
| WM239 | 49.8 ± 1.8 | 9.5 ± 0.9 | (19) | 19.7 ± 1.2 | (40) | 4.4 ± 0.4 | (9) |
| FM516-SV | 21.2 ± 1.7 | 7.8 ± 1.0 | (37) | 12.7 ± 1.8 | (60) | 6.2 ± 0.6 | (29) |

[a]Cells were seeded at 5 × 10$^4$ cells per 35-mm tissue culture plate and 24 h later the medium was changed with the indicated compounds, control = medium without additions, IFN-β = 2000 U/ml, MEZ = 10 ng/ml, and IFN-β + MEZ = 2000 U/ml + 10 ng/ml. Cell numbers were determined by Coulter Counter after 96-h growth. Results are the average of triplicate plates ± S.D. Bold values in brackets indicate percent of control growth.

Figure 3:
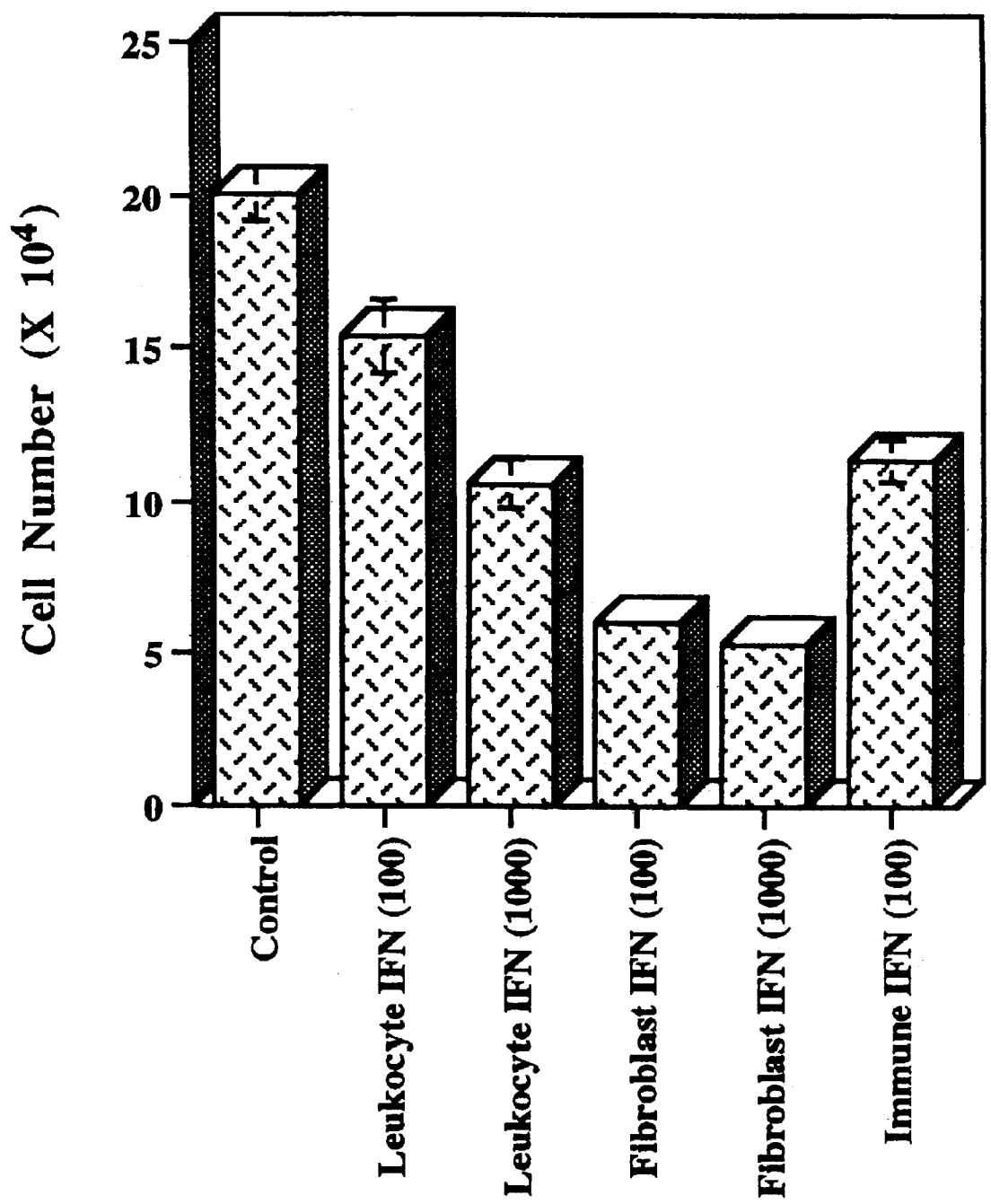
FIG. 3. Effect of interferons on growth of HO-1 cells. Cells were grown for 96 h in the absence or presence of IFN-α (100 and 1000 U/ml), IFN-β (100 and 1000 U/ml) or IFN-γ(100 U/ml) and cell numbers in triplicate plates were determined. Results are the average cell number±S.D. from the mean.
Figure 4:
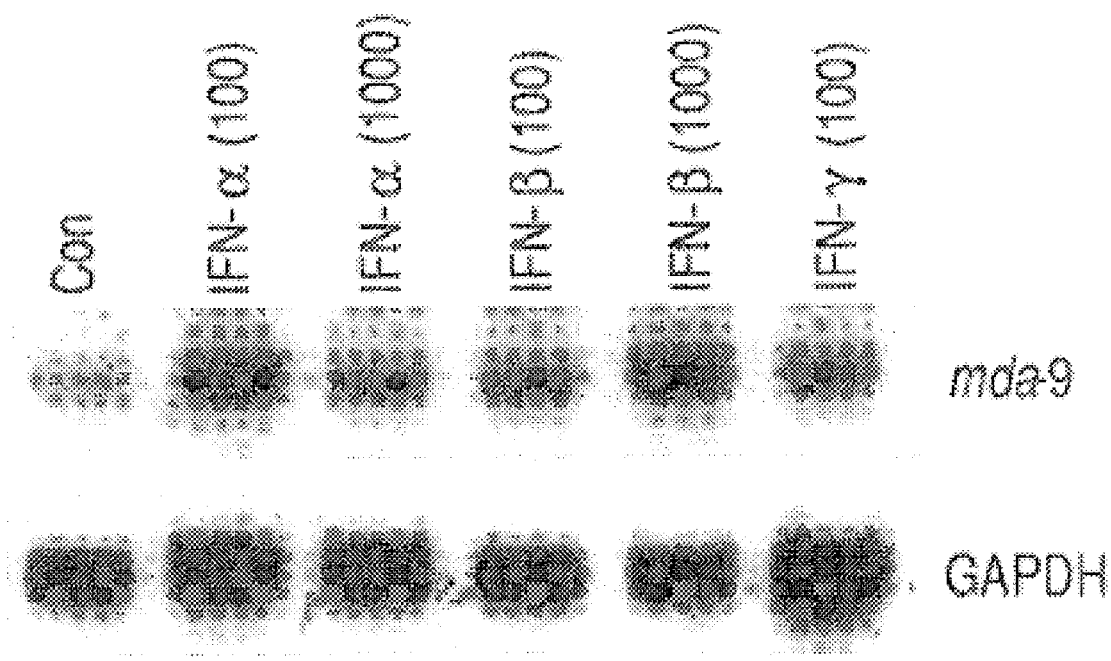
FIG. 4. Effect of interferons on mda-9 expression in HO-1 cells. HO-1 cells were grown for 96 h in the absence or presence of IFN-α (100 and 1000 U/ml), IFN-β (100 and 1000 U/ml) or IFN-γ(100 U/ml) and RNA was analyzed as described in FIG. 1.
Figure 5:
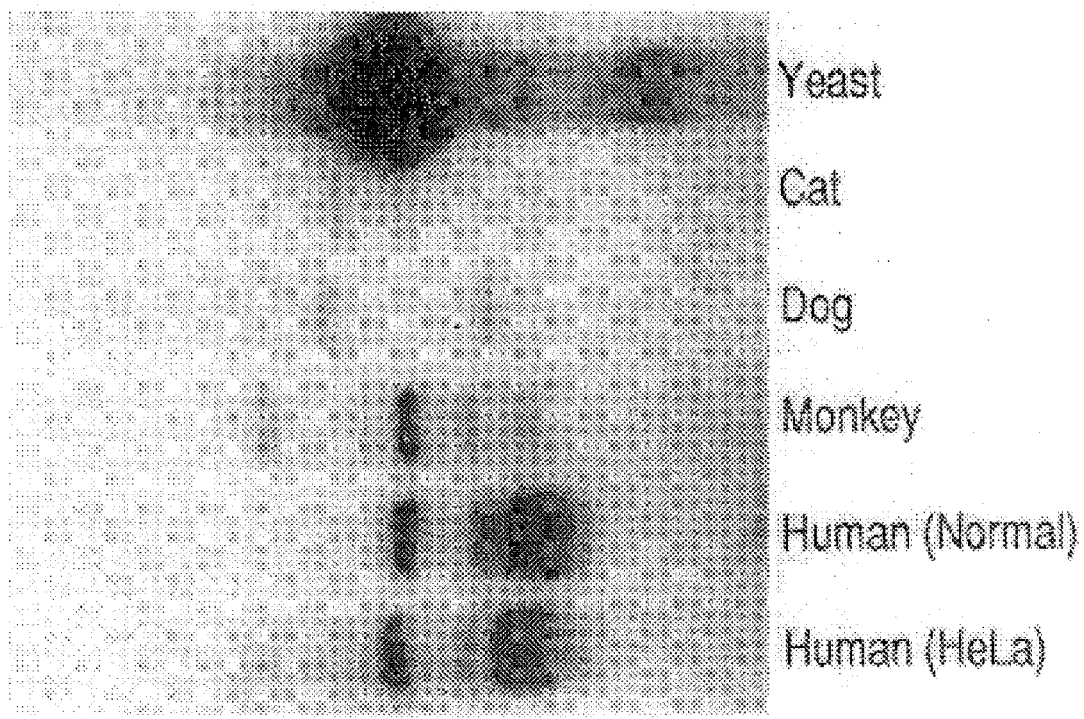
FIG. 5. Evolutionary conservation of the genomic mda-9 sequences. Genomic DNA (8 μg) isolated from different species, yeast (*Saccharomyces cerevisiae*), cat, dog, monkey (Rhesus) and human (normal and HeLa), were digested with HindIII. The digested DNAs were electrophoresed, transferred to nylon filters, hybridized with $^{32}$p-labeled mda-9 gene probe and exposed to autoradiography.
Figure 6:
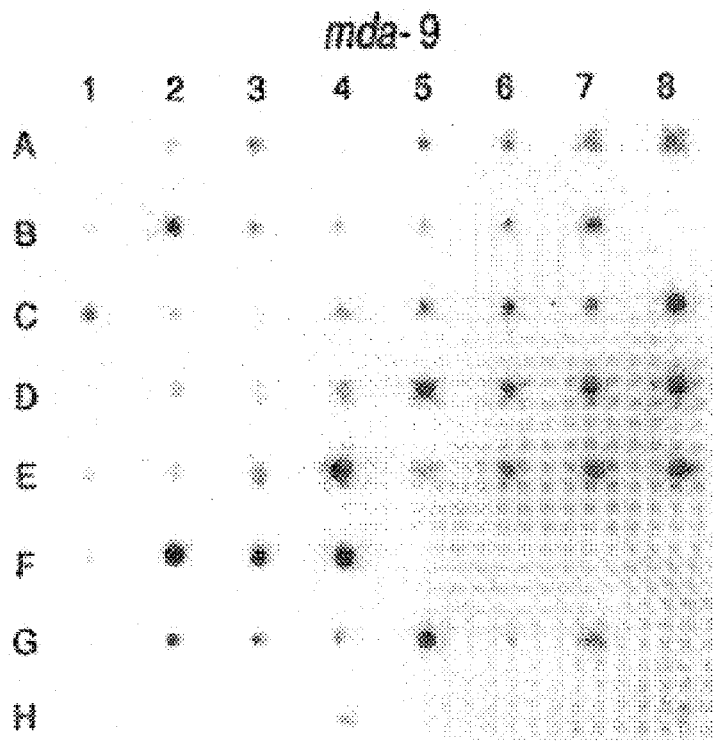
FIG. 6. Expression of mda-9 in human tissues. A positively charged nylon membrane containing poly A$^+$ RNAs from the 50 tissues indicated was hybridized with an mda-9 probe and exposed to autoradiography. The nylon membrane was stripped, reprobed with a ubiquitin probe and exposed to autoradiography.
Figure 6B:
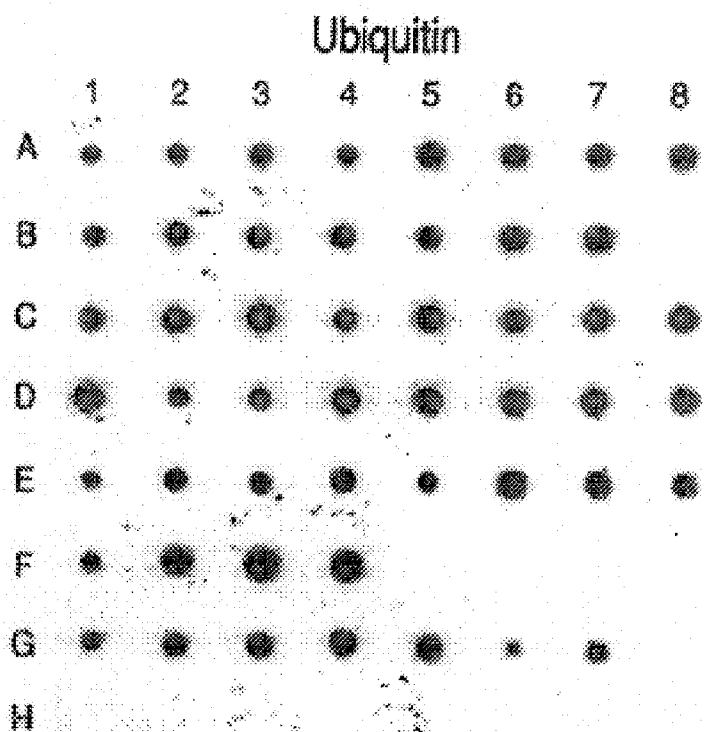

Treatment of HO-1 Cells with Interferon Induces Growth Suppression While Enhancing mda-9 Expression. Experiments were performed to determine if a relationship exists between growth suppression and reduced mda-9 expression. To test this connection, the effect of interferon and MEZ treatment on proliferation and mda-9 expression in human melanoma cells was determined. Growth of HO-1 cells in the presence of type I interferon, IFN-α or IFN-β, or type II interferon, IFN-γ, suppresses the growth of HO-1 cells (FIG. 3). IFN-β is the most effective interferon in inhibiting HO-1 growth, with an ~70% reduction after 4 d treatment with 100 U/ml. Under similar experimental conditions, 100 U/ml of IFN-γ reduces growth by ~43% and 100 U/ml of IFN-α reduces growth by only ~23%. Unlike IFN-β+MEZ, which reduce mda-9 expression in HO-1 cells, all three interferons enhance mda-9 expression ~1.9- to ~4.0-fold based on equalization for GAPDH expression (FIG. 4). In contrast, mda-9 expression is unaffected in HO-1 cells grown for 4 days in 10 ng/ml of MEZ, even though growth is reduced by ~74% (Table 1 and data not shown). These results indicate that growth suppression in HO-1 cells can be dissociated from decreased mda-9 expression.

mda-9 Is an Evolutionary Conserved Gene. To determine if sequences homologous to human mda-9 are present in the genomes of other species Southern blotting analyses were performed using genomic DNAs from *Saccharomyces cerevisiae* (yeast), cat, dog, Rhesus monkey and human (normal and HeLa) (18) (FIG. 5). On the basis of intensity of hybridization in Southern blots, the greatest sequence homology occurs between monkey and human genomic DNAs. Hybridization with yeast DNA is also evident. The apparently high level of hybridization with the mda-9 probe is the result of an ~10-fold higher relative concentration of genomic yeast DNA added to this gel. Dog and cat genomic DNA display weaker hybridization after probing Southern blots with mda-9. These findings suggest that mda-9 is an evolutionary conserved gene. mda-9 Is Expressed in Diverse Human Tissues. To determine the pattern of expression of the mda-9 gene a Human RNA Master Blot™ that contains poly $A^+$ RNAs from 50 human tissues immobilized in separate dots on a nylon membrane was analyzed (FIG. 6). As a positive control for RNA expression the membranes were stripped and rehybridized with a ubiquitin cDNA probe (FIG. 6). Both mda-9 and ubiquitin are expressed in all 50 human tissues. Comparing the intensity of hybridization between mda-9 and ubiquitin, elevated expression of mda-9 occurs in putamen, adult spleen and fetal spleen and reduced expression occurs in whole brain, amygdala, caudate nucleus, cerebellum, cerebral cortex, frontal lobe, hippocampus, medulla oblongata, occipital lobe, substantia nigra, temporal lobe, thalamus, sub-thalamic nucleus, spinal cord, heart, aorta, skeletal muscle, colon, bladder, uterus, prostate, stomach, testis, ovary, pancreas, pituitary gland, adrenal gland, thyroid gland, salivary gland, mammary gland, kidney, liver, small intestine, thymus, peripheral blood leukocytes, lymph node, bone marrow, appendix, lung, trachea and placenta. mda-9 and ubiquitin are also expressed in fetal brain, fetal heart, fetal kidney, fetal liver, fetal thymus and fetal lung. Hybridization with mda-9 also occurs with *Escherichia coli* DNA and with human genomic DNA (500 ng) (FIG. 6). Longer exposures of the Human Master RNA Blot™ probed with ubiquitin indicates hybridization to human genomic DNA (both 100 and 500 ng), but no hybridization with *Escherichia coli* DNA (data not shown). No hybridization is observed with mda-9 or ubiquitin with yeast total RNA, yeast tRNA, *Escherichia coli* rRNA or poly r(A). The ability of mda-9 to hybridize to *Escherichia coli* suggests some homology to bacterial sequences. DNA data bank sequence searches indicate only minor homology within small regions of mda-9 and bacterial sequences. The ability of mda-9 to hybridize with human genomic DNA may indicate the presence of repetitive sequences or that this gene is highly abundant or a member of a multi-gene family. Analysis of multiple human tissue Northern blots also demonstrates fairly uniform mda-9 expression in multiple tissue types (data not shown).

Experimental Discussion

The aberrant differentiation/modified gene expression model of cancer development is based on the hypothesis that specific forms of cancer may develop from defects in differentiation and gene expression that are inherently reversible (6–11,13,14). If these assumptions are correct, then it may be possible to induce the appropriate program of gene expression and a more normal differentiated phenotype in a cancer cell by treatment with the appropriate agent (s) This idea has been experimentally tested using cultured human melanoma cells (13,14,16). The combination of IFN-β+MEZ results in changes in the expression of a spectrum of genes, including cell cycle and growth regulating genes, and the induction of an irreversible loss in proliferative ability and terminal differentiation in malignant melanoma cells (13–18,34). By using the molecular approach of subtraction hybridization those changes in gene expression that correlate with and may control growth and differentiation in human cancer cells are being defined (16–20). This information offers potential for identifying potentially new cellular targets for the differentiation therapy of human cancer.

In the present study a novel mda-9 gene identified by subtraction hybridization that is down-regulated when human melanoma cells are induced to terminally differentiate is described. Decreased expression of mda-9 in HO-1 cells can be distinguished from growth suppression or induction of specific markers of differentiation, such as enhanced melanin synthesis and the formation of dendrite-like processes. For example, agents that suppress growth in HO-1 cells without inducing markers of differentiation, such as IFN-γ, elevate mda-9 expression, whereas MEZ, which can reversibly induce elevated melanin synthesis, growth suppression and dendrite-like processes in HO-1 cells, has no effect on mda-9 expression. These findings suggest that mda-9 may be a component of the terminal differentiation program in human melanoma cells. Southern blotting using genomic DNAs from different species indicates that mda-9 is an evolutionary conserved gene and analysis of multiple human tissue-derived mRNAs indicate that mda-9 is a widely expressed gene, with a small elevation in expression in the putamen (brain) and spleen (both adult and fetal). Nucleotide and amino acid sequence analysis of mda-9 indicate no significant homology to previously reported genes. However, two small stretches of homology, 22 of 69 (31%) and 11 of 45 (24%) identities and 36 of 69 (52%) and 22 of 29 (75%) positives, respectively, are apparent between mda-9 (aa 196 to 264 and aa 135 to 179) and the X11 gene product (aa 637 to 705 and 554 to 598) (37). The X11 gene encodes a protein that is expressed in the brain, primarily in the granular layer of the cerebellum, but is not detectable in several non-neuronal tissues and cell lines. The X11 gene encodes a protein of 708-aa with a putative transmembrane segment and may represent a candidate Friedreich ataxia gene (37). Since the homologies between mda-9 and X11 are so small, it is unlikely that these genes display functional similarities.

Further studies are required to determine the biological relevance of modified mda-9 expression in terminal differentiation in human melanoma cells. For example, overexpression of mda-9 in melanoma cells could be used to determine if preventing down-regulation of mda-9 can modify the differentiation process. Alternatively, inhibiting mda-9 expression by using antisense based technologies can also be used to evaluate the role of this gene in terminal differentiation in human melanoma cells. Additional studies are also required to determine if altered mda-9 expression is associated with the differentiation or growth processes in other cancer and normal cell types. Experiments to determine the spectrum of cytokine and differentiation-modulating agents that can affect mda-9 expression will also be informative.

The gene expression changes associated with and mediating terminal differentiation in human melanoma cells are complex, consisting of both increases and decreases in the abundance of specific RNA species (10–12,14–20,34). Unraveling the roles of those gene products that positively regulate differentiation phenotypes and that negatively regulate growth is essential in order to define terminal differentiation on a molecular level. Several models are possible for integrating these gene changes in the terminal differentiation process. A 'master-switch' gene may exist that can singularly induce the cascade of gene expression changes resulting in terminal differentiation, i.e., differentiation is a linear process initially controlled by a single genetic element. Treatment of cells with an agent(s) that induces terminal differentiation may result in the induction and suppression of parallel sets of genes that ultimately converge to induce terminal differentiation, i.e., differentiation involves multiple independent pathways resulting in the activation of common genes mediating terminal differentiation. Alternatively, several independent and overlapping pathways may control differentiation, i.e., differentiation involves feedback loops consisting of multiple genes that display either elevated or decreased expression and that control the expression of downstream genes and pathways critical for differentiation. Further studies should help clarify the molecular and biochemical processes that control the induction and maintenance of terminal differentiation in human melanoma cells and delineate the roles of specific mda genes in regulating these processes.

References For First Series of Experiments

1. Fisher, P. B., Enhancement of viral transformation and expression of the transformed phenotype by tumor promoters. In: T. J. Slaga, Ed., Tumor Promotion and Cocarcinogenesis In Vitro, Mechanisms of Tumor Promotion, pp. 57–123, CRC Press, Boca Raton, Fla., 1984.
2. Bishop, J. M., Molecular themes in oncogenesis. Cell, 64: 235–248, 1991.
3. Vogelstein, B., and Kinzler, K. W., The multistep nature of cancer. Trends Genet., 9: 138–141, 1991.
4. Knudson, A. G., Antioncogenes and human cancer. Proc. Natl. Acad. Sci. U.S.A., 90: 10914–10921, 1993.
5. Hartwell, L. H., and Kastan, M. B., Cell cycle control and cancer. Science, 266: 1821–1828, 1994.
6. Waxman, S., Rossi, G. B., and Takaku, F., Eds., The Status of Differentiation Therapy, Vol. 1, Raven Press, New York, 1988.
7. Fisher, P. B., and Rowley, P. T., Regulation of growth, differentiation and antigen expression in human tumor cells by recombinant cytokines: applications for the differentiation therapy of cancer. In: Waxman, S., Rossi, G. B., and Takaku, F., Eds., The Status of Differentiation Therapy of Cancer, Vol. 2, pp. 201–213, Raven Press, New York, 1991.
8. Waxman, S., Rossi, G. B., and Takaku, F., Eds., The Status of Differentiation Therapy, Vol. 2, Raven Press, New York, 1991.
9. Waxman, S., Ed., Differentiation Therapy, Challenges in Molecular Medicine, Vol. 10, Ares-Serono Symposia Publications, Rome, Italy, 1995.
10. Chellappan, S. P., Giordano, A., and Fisher, P. B., The role of cyclin dependent kinases and their inhibitors in cellular differentiation and development. Current Topics in Microbiology and Immunology, Springer-Verlag, N.Y., in press, 1996.
11. Jiang, H., Lin, J., and Fisher, P. B., A molecular definition of terminal differentiation in human melanoma cells. Mol. Cell. Different., 2 (3): 221–239, 1994.
12. Jiang, H., Lin, J., Su, Z.-z., and Fisher, P. B., The melanoma differentiation associated gene-6 (mda-6), which encodes the cyclin-dependent kinase inhibitor p21, may function as a negative regulator of human melanoma growth and progression. Mol. Cell. Different., 4 (1):67–89, 1996.
13. Fisher, P. B., Prignoli, D. R., Hermo, H., Jr., Weinstein, I. B., and Pestka, S., Effects of combined treatment with interferon and mezerein on melanogenesis and growth in human melanoma cells. J. Interferon Res., 5: 11–22, 1985.
14. Jiang, H., Su, Z.-z., Boyd, J., and Fisher, P. B., Gene expression changes associated with reversible growth suppression and the induction of terminal differentiation in human melanoma cells. Mol. Cell. Different., 1 (1): 41–66, 1993.
15. Jiang, H., Lin, J., Young, S.-m., Goldstein, N. I., Waxman, S., Davila, V., Chellappan, S. P., and Fisher, P. B., Cell cycle gene expression and E2F transcription factor complexes in human melanoma cells induced to terminally differentiate. Oncogene, 11: 1179–1189, 1995.
16. Jiang, H., and Fisher, P. B., Use of a sensitive and efficient subtraction hybridization protocol for the identification of genes differentially regulated during the induction of differentiation in human melanoma cells. Mol. Cell. Different., 1 (3): 285–299, 1993.
17. Jiang, H., Lin, J., Su, Z.-z., Herlyn, M., Kerbel, R. S., Weissman, B. E., Welch, D. R., and Fisher, P. B., The melanoma differentiation-associated gene mda-6, which encodes the cyclin-dependent kinase inhibitor p21, is differentially expressed during growth, differentiation and progression in human melanoma cells. Oncogene, 10: 1855–1864, 1995.
18. Jiang, H., Lin, J. J., Su, Z.-z., Goldstein, N. I., and Fisher, P. B., Subtraction hybridization identifies a novel melanoma differentiation associated gene, mda-7, modulated during human melanoma differentiation, growth and progression. Oncogene, 11: 2477–2486, 1995.
19. Jiang, H., Lin, J. J., Tao, J., and Fisher, P. B., Suppression of human ribosomal protein L23A expression during cell growth inhibition by interferon-β. oncogene, 14, in press, 1997.
20. Jiang, H., Lin, J., Su, Z.-z., Collart, F. R., Huberman, E., and Fisher, P. B., Induction of differentiation in human promyelocytic HL-60 leukemia cells activates p21, WAF1/CIP1, expression in the absence of p53. Oncogene, 9:3397–3406, 1994.
21. Giovanella, B. C., Stehlin, J. S., Santamaria, C., Yim, S. O., Morgan, A. C., Williams, L. J., Leibovitz, A., Fialkow, P. Y., and Mumford, D. M., Human neoplastic and normal cells in tissue culture. I. Cell lines derived from malignant melanomas and normal melanocytes. J. Natl. Cancer Inst., 56: 1131–1142, 1976.
22. Huberman, E., Heckman, C., and Langenbach, R., Stimulation of differentiated functions in human melanoma cells by tumor-promoting agents and dimethyl sulfoxide. Cancer Res., 39: 2618–2624, 1979.
23. Melber, K., Zhu, G., and Diamond, L., SV40-transformed human melanocyte sensitivity to growth inhibition by the phorbol ester 12-0-tetradecanoylphorbol-13-acetate. Cancer Res., 49: 3650–3655, 1989.
24. Herlyn, M., Human melanoma: development and progression. Cancer Metastasis Rev., 9: 101–112, 1990.
25. Frohman, M. A., Dush, M. K, and Martin, G. R., Rapid production of full-length cDNAs from rare transcripts: amplification using a single gene-specific oligonucleotide primer. Proc. Natl. Acad. Sci. U.S.A., 85: 8998–9002, 1988.
26. Loh, E. Y., Elliot, J. F., Cwirla, S. A., Lanier, L. L., and Davis, M. M., Polymerase chain reaction with single-sided specificity: analysis of T cell receptor delta chain. Science, 243: 217–220, 1989.

27. Ohara, O., Dorit, R. L., and Gilbert, W., Direct genomic sequencing of bacterial DNA: the pyruvate kinase 1 gene of *Escherichia coli*. Proc. Natl. Acad. Sci. U.S.A., 86: 6883–6887, 1989.
28. Sanger, F., Nicklen, S., and Coulson, A. R., DNA sequencing with chain-terminating inhibitors. Proc. Natl. Acad. Sci. U.S.A., 74: 5463–5467, 1977.
29. Su, Z.-z., Leon, J. A., Jiang, H., Austin, V. A., Zimmer, S. G., and Fisher, P. B., Wild-type adenovirus type 5 transforming genes function as trans-dominant suppressors of oncogenesis in mutant adenovirus type 5 transformed rat embryo fibroblast cells. Cancer Res., 53: 1929–1938, 1993.
30. Reddy, P. G., Graham, G. M., Datta, S., Guarini, L., Moulton, T. A., Jiang, H., Gottesman, M. M., Ferrone, S., and Fisher, P. B., Effect of recombinant fibroblast interferon and recombinant immune interferon on growth and the antigenic phenotype of multidrug-resistant human glioblastoma multiforme cell. J. Natl. Cancer Inst., 83: 1307–1315, 1991.
31. Su, Z.-z., Grunberger, D., and Fisher, P. B., Suppression of adenovirus type 5 E1A-mediated transformation and expression of the transformed phenotype by caffeic acid phenethyl ester (CAPE). Mol. Carcinog., 4: 231–242, 1991.
32. Jiang, H., Su, Z.-z., Datta, S., Guarini, L., Waxman, S., and Fisher, P. B., Fludarabine phosphate selectively inhibits growth and modifies the antigenic phenotype of human glioblastoma multiforme cells expressing a multidrug resistance phenotype. Intl. J. Oncol., 1: 227–239, 1992.
33. Fort, P., Marty, L., Piechaczyk, M., Sabrouty, S. E., Dani, C., Jeanteur, P., and Blanchard, J. M., Various rat adult tissues express only one major mRNA species from the glyceraldehyde-3-phosphate-dehydrogenase multigenic family. Nucleic Acids Res., 13: 1431–1442, 1985.
34. Jiang, H., Waxman, S., and Fisher, P. B., Regulation of c-fos, c-jun, and jun-B gene expression in human melanoma cells induced to terminally differentiate. Mol. Cell. Different., 1 (2): 197–214, 1993.
35. Mark, D. B., Lu, S. D., Creasey, A., Yamamoto, R., and Lin, L., Site-specific mutagenesis of the human fibroblast interferon gene. Proc. Natl. Acad. Sci. U.S.A., 81: 5662–5666, 1984.
36. Rehberg, G., Kelder, B., Hoal, E. G., and Pestka, S., Specific molecular activities of recombinant and hybrid leukocyte interferons. J. Biol. Chem., 257: 11497–11502, 1982.
37. Duclos, F., Boschert, U., Sirugo, G., Mandel, J.-L., Hen, R., and Koenig, M., Gene in the region of the Friedreich ataxia locus encodes a putative transmembrane protein expressed in the nervous system. Proc. Natl. Acad. Sci. U.S.A., 90: 109–113, 1993.

SECOND SERIES OF EXPERIMENTS

Subtraction hybridization using a cDNA library prepared from temporally spaced mRNAs from human melanoma cells treated with recombinant human fibroblast interferon (IFN-β) plus mezerein (MEZ) that induces terminal differentiation (tester cDNA library) and a temporally spaced cDNA library prepared from actively proliferating melanoma cells (driver cDNA library) produced a Temporally spaced Subtracted (TSS) cDNA library. This approach resulted in the identification of melanoma differentiation associated (mda) genes displaying both enhanced and suppressed expression during growth inhibition and differentiation. In the present report, we describe a novel cDNA mda-9 that consists of 2,084 nucleotides, and encodes a protein of 298 amino acids with a predicted $M_r$ of ~33 kDa. Treatment of human SV40-immortalized normal melanocytes, early radial growth phase primary melanoma and metastatic melanoma cells with immune interferon, IFN-γ, induces growth suppression and enhances mda-9 expression without inducing terminal differentiation. These results establish that induction of terminal differentiation in human melanoma cells, using the combination of a type I interferon (IFN-β)+MEZ, can elicit signaling pathways and gene expression changes also regulated by type II immune interferon.

Treatment of metastatic human melanoma cells with the combination of IFN-β and the antileukemic compound MEZ results in an irreversible loss of proliferative ability and terminal cell differentiation (Fisher et al., 1985; Jiang et al., 1993). To define the gene expression changes that mediate these phenomena we have used an efficient subtraction hybridization approach (Jiang and Fisher, 1993; Jiang et al., 1995a, 1995b). Since the precise spatial kinectics of the specific gene expression changes involved in inducing terminal differentiation in chemically treated HO-1 human melanoma cells are not known, our cloning strategy involved the use of pooled mRNAs collected at various times after treatment with IFN-β+MEZ, i.e., 2, 4, 8, 12 and 24 hr, to construct a tester cDNA library. A second cDNA library was generated from mRNAs isolated over the same time periods from actively growing HO-1 human melanoma cells and this temporally spaced driver cDNA library was subtracted from the temporally spaced tester cDNA library, thereby producing a differentiation-inducer treated TSS human melanoma cDNA library (Jiang and Fisher, 1993; Lin et al., 1996).

Seventy random cDNA clones were isolated from the differentiation-inducer treated TSS human melanoma cDNA library (representing ~2.5% of the total subtracted cDNA library) resulting in 23 clones displaying elevated expression after exposure to the inducing agent(s), IFN-βMEZ and/or IFN-β+MEZ (Jiang and Fisher, 1993). This approach resulted in the cloning of 9 originally novel mda genes, not previously reported in DNA data bases. Subsequent studies indicate that the unique mda-6 gene which is upregulated during growth arrest and terminal differentiation in human melanoma cells is identical to the cyclin dependent kinase inhibitor p21, also identified as Waf1, Cip1 and Sdi1 (Jiang et al., 1994, 1995b, 1996a). A novel gene mda-7 that is also elevated in terminally differentiated human melanoma cells is a ubiquitous inhibitor of cancer growth (Jiang et al., 1995b, 1996b). The mda-20 gene is the human ribosomal protein L23a gene that is down-regulated following treatment with IFN-β (Jiang et al., 1997). The novel mda-9 gene displays decreased expression as a function of induction of irreversible growth suppression and terminal differentiation in several human melanoma cell lines (Lin et al., 1996).

In the present study we demonstrate that mda-9 expression is elevated following IFNγ treatment in human melanocyte and melanoma cell lines, even though growth is suppressed. This observation is unanticipated and suggests that type II interferon responsive genes may be up-regulated as a function of induction of terminal differentiation by human IFN-β (a product of the type I interferon gene) in combination with MEZ. Furthermore, the direction of a specific gene expression change in growth suppressed human melanoma is dependent on the inducing agent and is subject to either increased or decreased expression. In this context, terminal differentiation clearly involves complex pathways with overlapping convergent and divergent gene expression changes that can also be elicited after exposure to specific cytokines, such as IFN-γ.

EXPERIMENTAL DETAILS

Materials and Methods

Cell lines and culture conditions. HO-1 is a melanotic melanoma cell line produced from a metastatic inguinal node lesion from a 49-year-old female and was used between passages 170 and 200 (Giovanella et al., 1976; Huberman et al., 1979; Fisher et al., 1985). C8161 is a highly metastatic amelanotic human melanoma cell line derived from an abdominal wall metastasis (Welch et al., 1991). FM516-SV is a normal human melanocyte culture immortalized by the SV40 T-antigen gene (Melber et al., 1989). The WM35 cell line was isolated from a patient with a radial growth phase primary melanoma (Herlyn, 1990). The WM278 cell line is from a patient with an early vertical growth phase primary melanoma (Herlyn, 1990). Cultures were grown at 37° C. In a 95% air 5% $CO_2$-humidified incubator in Dulbecco's modified Eagle's medium (DMEM) supplemented with 5 or 10% fetal bovine serum. Cultures were maintained in the logarithmic phase of growth by subculturing (1:5 or 1:10) prior to confluence approximately every 4 to 7 D.

Subtraction hybridization, RACE and sequence analysis. Identification and cloning of mda-9 was accomplished as described previously (Jiang and Fisher, 1993). Briefly, a cDNA library was prepared from RNA isolated from actively growing HO-1 cells (driver) and RNAs isolated from HO-1 cells treated with IFN-β+MEZ (2000 U/ml+10 ng/ml) for 2, 4, 8, 12, and 24 hr (temporally spaced tester). Subtraction hybridization was then performed between double-stranded tester DNA and single-stranded driver DNA prepared by mass excision of the libraries. The TSS cDNAs were efficiently cloned into the λ Uni-ZAP phage vector and used to screen Northern blots containing total RNA isolated from control HO-1 cells and HO-1 cultures treated for 24 hr with IFN-β (2000 U/ml), MEZ (10 ng/ml) or IFN-β+MEZ (2000 U/ml+10 ng/ml). This strategy resulted in the identification of a partial mda-9 cDNA (Jiang et al., 1994). A full-length mda-9 cDNA was isolated following screening of a differentiation inducer-treated HO-1 cDNA library (Jiang and Fisher, 1993) and using the procedure of rapid amplification of cDNA ends (RACE) as described previously (Jiang et al., 1995b). Sequence analysis was determined as described (Sanger et al., 1977).

RNA isolation and northern blotting. Total cellular RNA was isolated by the guanidinium/phenol procedure, and Northern blotting was performed as described (Reddy et al., 1991; Su et al., 1991). Ten micrograms of RNA were denatured with glyoxal/dimethyl sulfoxide (DMSO), electrophoresed in 1.0% agarose gels, transferred to nylon membranes, and hybridized with a $^{32}$P-labeled mda-9 probe. After stripping the membranes were hybridized to a $^{32}$P-labeled rat GAPDH probe (Fort et al., 1985) as described previously (Reddy et al., 1991; Su et al., 1991). Following hybridization, the filters were washed and exposed for autoradiography. RNA blots were quantitated by densitometric analysis using a Molecular Dynamics densitometer (Sunnyvale, Calif.) (Jiang et al., 1993).

Recombinant human gamma interferon. Recombinant human IFN-γ was kindly provided by Dr. Sidney Pestka (UMDNJ-Robert Wood Johnson Medical School, N.J.). The interferon titer was determined using a cytopathic effect inhibition assay with VSV on the human WISH cell line (Rehberg et al., 1982).

Experimental Results

Subtraction hybridization identifies mda-9 as a component of the terminal differentiation pathway in human melanoma cells.

Subtraction hybridization represents an effective experimental approach for identifying and cloning genes displaying differential expression. This strategy has been applied to human melanoma cells induced to terminally differentiate by treatment with IFN-β+MEZ resulting in the cloning of mda genes (Jiang and Fisher, 1993). We presently describe properties of mda-9, a novel cDNA of 2,084 nucleotides (Lin et al., 1996) with sequence homology to a recently reported human scaffold protein Pbp1 gene (U83463; deposited Jan. 1, 1997) (FIG. 7A) (Accession # AF006636). In vitro translation confirms that mda-9 encodes a putative protein with a predicted $M_r$ of ~33 kDa (data not shown). Tissue distribution analysis indicates that mda-9 is widely expressed in diverse tissues, with slightly elevated expression in brain (putamen) and spleen (adult and fetal) (Lin et al., 1996). Southern blot analysis documents that mda-9 is a well-conserved gene with a homologous sequence present in yeast (Lin et al., 1996).

With the aid of the GCG computer package (Genetics Computer Group, Madison, Wis.), the mda-9 sequence was analyzed. An open reading frame (ORF) is designated to a region from nucleotide (nt) 76 to 972 which starts at a methionine codon located in the context relative to the Kozak consensus sequence (Kozak, 1987). The ORF encodes a 298 amino acid (aa) protein (FIG. 7) with a predicted mass of 32.48 kDa as confirmed by an in vitro translation assay (data not shown). The predicted mda-9 protein contains two possible protein kinase C (PKC) phosphorylation sites at aa 171 and 189, five possible casein kinase II phosphorylation sites at aa 6, 60, 97, 189, 289, and 294, one possible tyrosine phosphorylation site at aa 48, and seven possible myristylation sites at aa 58, 80, 98, 102, 151, 248, and 262. A transmembrane segment from aa 257 to 276 can be anticipated based on the strong tendency of the amino acid sequence to form transmembrane helices. No homology to other motifs were found. Recently, a cDNA sequence was deposited in Genbank as a scaffold protein (Pbp1) (U83463), that is identical to mda-9 except that it is shorter than the mda-9 cDNA by 87 bp. No reference to the putative function of the Pbp1 gene is provided.

The mda-9 ORF is flanked by 5' untranslated region of 75 bp and 3' untranslated region of 1096 bp, respectively. There is no additional ATG codon in the 5' untranslated region. We were unable to obtain cDNAs with longer 5'-leader sequences by the RACE technique, suggesting that the 5'-end of the mda-9 sequence is the transcription initiation site. The 3' untranslated region contains one consensus element (ATTTA, nt 1390) involved in mRNA instability (Shaw and Kamen, 1986). No match to the consensus poly (A) signal sequence (AATAAA) is present, suggesting that a variant of the polyadenylation signal, AATTAA at nt 2051, serves this function (Wickens and Stephenson, 1984).

Effect of IFN-γ on Melanocyte and Melanoma Cell Growth and Expression of mda-9

Figure 8:
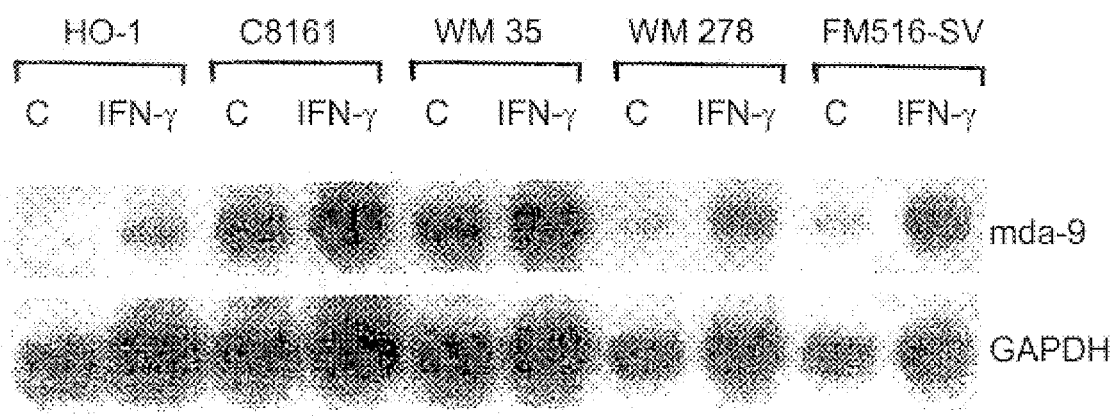
FIG. 8. Effect of recombinant human gamma interferon (IFN-γ) on mda-9 expression in human melanocyte and melanoma cell lines. The indicated cell typed were grown for 96 hr in the absence (C) or presence of 100 U/ml of IFN-γ. Total RNA was isolated and analyzed by Northern blotting. Filters were probed with mda-9 then stripped and probed with GAPDH. The cell lines used include: HO-1 and C8161 from metastatic melanomas; WM35 from a RGP (radial growth phase) primary melanoma; WM278 from an early VGP (vertical growth phase) primary melanoma; and FM516-SV derived from a normal human melanocyte culture immortalized by the SV40 T-antigen gene.

IFN-γ inhibits the growth of SV40-transformed normal human melanocyte and human melanoma cells (Table 2). With specific cell types, even 1 U/ml of IFN-γ induces growth suppression. The proliferation inhibitory effects of IFN-γ are most pronounced in the melanocyte (FM516-SV) and the radial growth phase primary melanoma (WM35) cell lines (Table 2). In contrast to its effect on cell growth, IFN-γ variably stimulates mda-9 expression in the different cell lines. Increases in RNA levels range from ~1.7-fold to ~23.7-fold and vary between cell types and in different experiments (FIG. 8 and data not shown). No direct relationship is apparent between the degree of IFNγ induced growth inhibition and the relative level of increase in mda-9 mRNA expression. Enhanced mda-9 expression is apparent within 2 hr of exposure of HO-1 cells to 100 U/ml of recombinant human IFN-γ (FIG. 9A). The maximum increase in mda-9 RNA in HO-1 cells following IFNγ treatment occurs between 8 and 24 hr post-treatment. A similar pattern of increase is apparent in FM516-SV cells treated with 100 U/ml of IFNγ (data not shown). IFN-γ dose-response studies in human melanocyte/melanoma cells indicate that mda-9 regulation is extremely sensitive to this cytokine (FIG. (9B). Even with doses as low as 0.1 U/ml, mda-9 expression is elevated in HO-1 (FIG. 9B) and FM516-SV (data not shown) cells. Maximum enhancing effects are evident when HO-1 or FM516-SV cells are treated with 10 U/ml of IFN-γ.

pathway following treatment with IFN-γ and/or during the process of induction of terminal differentiation by treatment with IFN-β+MEZ.

The molecular determinants of growth control and terminal differentiation in human melanoma cells are beginning to be defined (Jiang et al., 1994). Mda-9 may represent an important element in these processes. Moreover, elucidation of the role of mda-9 in growth control, terminal differentiation and response to specific cytokines (such as IFN-γ) will prove valuable in mechanistically understanding these important physiological processes.

References for Second Series of Experiments

Bach, E. A., Aguet, M. and Schreiber, R. D. (1997) The IFNγ receptor: a paradigm for cytokine receptor signaling. Annu. Rev. Immunol. 15, 563–591.

TABLE 2

Effect of recombinant immune interferon (IFN-γ) on the growth of normal human melanocyte and melanoma cell lines

| Experimental Conditions[a] | Cell Lines Analyzed | | | | | | | | |
|---|---|---|---|---|---|---|---|---|---|
| | FM516-SV | | WM35 | | WM278 | | HO-1 | | C8161 |
| Control | 20.7 ± 0.6 | | 86.5 ± 2.1 | | 22.0 ± 1.0 | | 20.3 ± 1.7 | | 34.8 ± 0.7 |
| 1 | 16.8 ± 0.5 (19) | | 84.8 ± 6.7 (2) | | 14.9 ± 0.8 (33) | | 15.8 ± 0.5 (220) | | 24.4 ± 0.4 (30) |
| 10 | 9.8 ± 0.6 (52) | | 62.7 ± 4.3 (28) | | 12.7 ± 1.0 (42) | | 15.4 ± 0.3 (24) | | 25.1 ± 0.8 (28) |
| 100 | 5.1 ± 0.3 (75) | | 28.2 ± 1.7 (67) | | 12.5 ± 0.6 (440) | | 11.5 ± 1.3 (44) | | 22.2 ± 1.4 (36) |

[a]Cells were seeded in triplicate in 35-mm tissue culture plates at $2 \times 10^4$ (FM516-SV, HO-1 and C8161) or $5 \times 10^4$ (WM35 and WM278), the medium was changed 24 hr later without additions (Control) or with 1, 10 or 100 U/ml of IFN-γ and cell numbers were determined 96 hr later. Results are the average cell number ± S.D. from the mean. Bold values in brackets indicate percent of cell number reduction versus control. FM516-SV, is a normal human melanocyte cell line immortalized by SV40; WM35 is a cell line produced from a patient with an early radial growth phase primary human melanoma; WM278, HO-1 and C8161, are cell lines established from metastatic human melanoma.

Experimental Discussion

Subtraction hybridization with temporally spaced mRNA samples permitted cloning of a novel gene, mda-9, that displays biphasic regulation during induction of irreversible growth suppression and terminal differentiation in human melanoma cells (Lin et al., 1996). Treatment of HO-1 cells with IFN-β+MEZ results in maximum increases in mda-9 RNA 8 to 12 hr post treatment and a reduction in mda-9 expression at 24 hr. The present study demonstrates that mda-9 is variably upregulated by recombinant human IFNγ in SV40-immortalized human melanocyte and human melanoma cells even though growth is suppressed. Maximum mda-9 levels are observed between 8 and 24 hr treatment with IFN-γ. These results document that the expression of mda-9 is subject to complex regulation in human melanocyte/melanoma lineage cells and the direction of the response, i.e., increase or decrease, is dependent on the inducing agent and the cellular program modified.

Recent studies are providing important insights into the signaling pathways involved in IFN-β regulation of gene expression (Darnell et al., 1994; Bach et al., 1997; Boehm et al., 1997). The current model for IFNγ induction of gene expression involves binding of IFN-γ to high affinity cell surface receptors, transphosphorylation and activation of JAK1 and JAK2 kinases and phosphorylation of STAT (signal transducers and activators of transcription) proteins. The phosphorylated STAT proteins migrate into the nucleus, binding to specific DNA elements (gamma-interferon activation site; GAS, containing 9 nucleotides with a consensus sequence of TTNCNNNAA) and direct transcriptional activation of IFN-γ-inducible genes. Further studies are required to determine if enhanced mda-9 expression occurs via this Boehm, U., Klamp, T., Groot, M. and Howard, J. C. (1997) Cellular responses to interferon-γ. Annu. Rev. Immunol. 15, 749–795.

Darnell, J. E., Kerr, I. M. and Stark, G. R. (1994) Jak-STAT pathways and transcriptional activation in response to IFNs and other extracellular signaling proteins. Science 264, 1415–1421.

Fisher, P. B., Prignoli, D. R., Hermo, H., Jr., Weinstein, I. B. and Pestka, S. (1985) Effects of combined treatment with interferon and mezerein on melanogenesis and growth in human melanoma cells. J. Interferon Res. 5, 11–22.

Fort, P., Marty, L., Piechaczyk, M., Sabrouty, S. E., Dani, C., Jeanteur, P. and Blanchard, J. M. (1985) Various rat adult tissues express only one major mRNA species from the glyceraldehyde-3-phosphate-dehydrogenase multigenic family. Nucleic Acids Res. 13, 1431–1442.

Giovanella, B. C., Stehlin, J. S., Santamaria, C., Yim, S. O., Morgan, A. C., Williams, L. J., Leibovitz, A., Fialkow, P. Y., and Mumford, D. M. (1976) Human neoplastic and normal cells in tissue culture. I. Cell lines derived from malignant melanomas and normal melanocytes. J. Natl. Cancer Inst. 56, 1131–1142.

Herlyn, M. (1990) Human melanoma development and progression. Cancer Metastasis Rev. 9, 101–112.

Huberman, E., Heckman, C., and Langenbach, R. (1979) Stimulation of differentiated functions in human melanoma cells by tumor-promoting agents and dimethyl sulfoxide. Cancer Res. 39, 2618–2624.

Jiang, H. and Fisher, P. B. (1993) Use of a sensitive and efficient subtraction hybridization protocol for the identification of genes differentially regulated during the induction of differentiation in human melanoma cells. Mol. Cell. Different. 1 (3), 285–299.

Jiang, H., Lin, J., and Fisher, P. B. (1994) A molecular definition of terminal differentiation in human melanoma cells. Mol. Cell. Different. 2 (3) 221–239.

Jiang, H., Lin, J., Su, Z.-z. and Fisher, P. B. (1996a) The melanoma differentiation associated gene-6 (mda-6), which encodes the cyclin-dependent kinase inhibitor p21, may function as a negative regulator of human melanoma growth and progression. Mol. Cell. Different. 4 (1), 67–89.

Jiang, H., Lin, J. J., Su, Z.-z., Goldstein, N. I. and Fisher, P. B. (1995a) Subtraction hybridization identifies a novel melanoma differentiation associated gene, mda-7, modulated during human melanoma differentiation, growth and progression. Oncogene 11, 2477–2486.

Jiang, H., Lin, J., Su, Z.-z., Herlyn, M., Kerbel, R. S., Weissman, B. E., Welch, D. R. and Fisher, P. B. (1995b) The melanoma differentiation-associated gene mda-6, which encodes the cyclin-dependent kinase inhibitor p21, is differentially expressed during growth, differentiation and progression in human melanoma cells. Oncogene 10, 1855–1864.

Jiang, H., Lin, J. J., Tao and Fisher, P. B. (1997) Suppression of human ribosomal protein L23A expression during cell growth inhibition by interferon-β. Oncogene 14, 473–480.

Jiang, H., Su, Z.-z. Boyd, J. and Fisher, P. B. (1993) Gene expression changes associated with reversible growth suppression and the induction of terminal differentiation in human melanoma cells. Mol. Cell. Different. 1 (1): 41–66.

Jiang, H., Su, Z.-z., Lin, J. J., Goldstein, N. I., Young, C. S. H. and Fisher, P. B. (1996b) The melanoma differentiation associated gene mda-7 suppresses cancer cell growth. Proc. Natl. Acad. Sci. USA 93: 9160–9165.

Jiang, H., Waxman, S. and Fisher, P. B. (1993) Regulation of c-fos, c-jun, and Jun-B gene expression in human melanoma cells induced to terminally differentiate. Mol. Cell. Different. 1 (2): 197–214.

Kozak, M. (1987) An analysis of 5'-noncoding sequences from 699 vertebrate messenger RNAs. Nucleic Acids Res. 15, 8125–8148.

Lin, J. J., Jiang, H. and Fisher, P. B. (1996) Characterization of a novel melanoma differentiation associated gene, mda-9, that is down-regulated during terminal cell differentiation. Mol. Cell. Different. 4 (4): 317–333.

Melber, K., Zhu, G. and Diamond, L. (1989) SV40-Transformed human melanocyte sensitivity to growth inhibition by the phorbol ester 12-O-tetradecanoylphorbol-13-acetate. Cancer Res. 49, 3650–3655.

Reddy, P. G., Graham, G. M., Datta, S., Guarini, L., Moulton, T. A., Jiang, H., Gottesman, M. M., Ferrone, S. and Fisher, P. B. (1991) Effect of recombinant fibroblast interferon and recombinant immune interferon on growth and the antigenic phenotype of multidrug-resistant human glioblastoma multiforme cells. J. Natl. Cancer Inst. 83, 1307–1315.

Rehberg, G., Kelder, B., Hoal, E. G. and Pestka, S. (1982) Specific molecular activities of recombinant and hybrid leukocyte interferons. J. Biol. Chem. 257, 11497–11502.

Sanger, F., Nicklen, S. and Coulson, A. R. (1977) DNA sequencing with chain-terminating inhibitors. Proc. Natl. Acad. Sci. USA 74, 5463–5467.

Su, Z.-Z., Grunberger, D. and Fisher, P. B. (1991) Suppression of adenovirus type 5 E1A-mediated transformation and expression of the transformed phenotype by caffeic acid phenethyl ester (CAPE). Mol. Carcinog. 4, 231–242.

Shaw, G. and Kamen, R. (1986). A consensus AU sequence form the 3' untranslated region of GM-CSF mRNA mediates selective mRNA degradation. Cell, 46, 659–667.

Welch, D. R., Bisi, J. E., Miller, B. E., Conaway, D., Seftor, E. A., Yokem, K. H., Gilmore, L. B., Seftor, R. E., Nakajima, M. and Hendrix, M. J. (1991) Characterization of a highly invasive and spontaneously metastatic human malignant melanoma cell line. Intl. J. Cancer, 47, 227–237.

Wickens, M. and Stephenson, P. (1984). Role of the conserved AAUAAA sequence: four AAUAAA point mutants prevent messenger RNA 3' end formation. Nature, 226, 1045–1051.

THIRD SERIES OF EXPERIMENTS

Previous experiments demonstrate that mda-9 expression occurs in 50 normal human tissues and various human cancer cell lines (1,2). Induction of terminal differentiation with an irreversible loss in proliferative ability in human melanoma cells by treatment with recombinant human fibroblast interferon (IFN-β) plus the antileukemic compound mezerein (MEZ) (3,4) results in a reduction in mda-9 expression (1). In contrast, treatment of the same cell types with various interferons, including IFN-β, recombinant human leukocyte interferon (IFN-α) and recombinant human immune interferon (IFN-γ), results in growth suppression and an elevation in mda-9 expression (1,2). The growth suppression effect is greatest with IFN-β, whereas the enhancement in mda-9 gene expression is greatest with IFN-γ. These results demonstrate that mda-9 expression can be modified by a number of diverse signals, including induction of differentiation and treatment with recombinant cytokines, that occur in a growth-independent manner.

To directly define a functional role for mda-9 in cellular physiology, pREP4 expression vectors were constructed that express mda-9 in either a sense orientation (pREP-mda-9 S) or an antisense orientation (pREP-mda-9 AS). Constructs were prepared as described previously in Jiang et al. (5–7). Experiments were then performed to determine the effect of altering mda-9 expression on the growth of HBL-100, an immortalized normal human breast epithelial cell line (containing SV40 sequences) and MCF-7, a human breast carcinoma cell line. The results of a representative study determining the effect of pREP4 (expression vector construct lacking the mda-9 gene), pREP-mda-9 S and pREP-mda-9 AS are shown in Table 3. In both cell types, forced expression of mda-9 in either a sense or antisense orientation inhibited colony formation. Inhibition was greatest in the two cell types when treated with AS mda-9. The effect on growth was greater in HBL-100 than in MCF-7 cells.

The studies briefly described above demonstrate that mda-9 directly contributes to cell growth. Interestingly, since both overexpression (mda-9 S) and inhibition in expression (mda-9 AS) modifies growth, it appears that mda-9 may function as a barometer for maintaining cellular homeostasis. If this hypothesis is correct strategies designed to modify mda-9 expression during treatment with various compounds may permit the use of this gene for therapeutic applications. For example, combining AS mda-9 expression (using a targeting vector such as an adenovirus, adeno-associated virus, retrovirus, vaccinia virus, Epstein Barr virus, etc.) (7,8) with agents capable of partially inducing differentiation, such as IFN-β or MEZ, but not terminal differentiation may permit the use of a single agent for differentiation therapy of cancer. Moreover, combining S mda-9 expression (using a targeting vector such as an adenovirus, adeno-associated virus, retrovirus, vaccinia virus, Epstein Barr virus, etc.) (7,8) in combination with specific cytokines, such as IFN-α, IFN-β, IFN-γ or TNF-α, DNA damaging chemotherapeutic agents (such as dactinomycin, cis-platinum, taxol and its analogs, etc.) or physical therapeutic agents (such as gamma irradiation) may result in enhanced growth suppression in tumor cells. These effects can be further augmented and targeted to specific cell types by using gene expression enhancers and tissue specific promoters. Experiments to confirm these possibilities are presently in progress.

TABLE 3

Effect of overexpression and an inhibition in expression of mda-9 on colony formation in monolayer culture of HBL-100 and MCF-7 cells.

| Cell Type[1] | Plasmid Transfect[2] | Colony Numbers[3] | % of Control[4] |
|---|---|---|---|
| HBL-100 | pREP4 | 913.75 ± 178.4 | 100 |
|  | pREP-mda-9 S | 258.5 ± 44.4 | 28.3 |
|  | PREP-mda-9 AS | 129.0 ± 30.3 | 14.1 |
| MCF-7 | pREP4 | 232.5 ± 12.5 | 100 |
|  | pREP-mda-9 S | 187.5 ± 16.1 | 80.7 |
|  | PREP-mda-9 AS | 134.75 ± 10.3 | 58.0 |

[1]HBL-100 is an immortal normal human breast epithelial cell line. However, this cell line contains SV40 sequences and at late passage can form colonies in agar and tumors in athymic nude mice. MCF-7 is a human breast carcinoma cell line.
[2]The different cell types were transfected with 10 μg of pREP4 (an expression vector containing an Rous sarcoma virus (RSV) promoter, a bacterial hygromycin resistance gene without an mda-9 gene insert), pREP-mda-9 S (a pREP4 vector containing in a sense orientation driven by an RSV promoter) or pREP-9 AS (a pREP4 vector containing an mda-9 gene cloned in an antisense orientation and driven by an RSV promoter) plasmid DNA.
[3]Approximateiy 48 hr after DNA transfection, cells were reseeded and selected for 3 weeks in medium containing hygromycin. Results are the average number of colonies from 4 plates ± standard deviation from the mean.

References for Third Series of Experiments.

1. Lin, J. J., Jiang, H., and Fisher, P. B. (1996) Characterization of a novel melanoma differentiation associated gene, mda-9, that is down-regulated during terminal cell differentiation. Mol. Cell. Different., 4(4):317–333.
2. Lin, J. J., Jiang, H., and Fisher (197) Melanoma differentiation associated gene-9, mda-9, is a human gamma interferon responsive gene. Gene, in press.
3. Fisher, P. B., Prignoli, D. R., Hermo, H., Jr., Weinstein, I. B. and Pestka, S. (1985) Effects of combined treatment with interferon and mezerein on melanogenesis and growth in human melanoma cells. J. Interferon Res. 5:11–22.
4. Jiang, H., Su, Z.-z., Boyd, J., and Fisher, P. B. (1993) Gene expression changes associated with reversible growth suppression and the induction of terminal differentiation in human melanoma cells. Mol. Cell. Different., 1(1):41–66.
5. Jiang, H., Lin, J., Su, Z-z., Herlyn, M., Kerbel, R. S., Weissman, B. E., Welch., D. R., and Fisher, P. B. (995) The melanoma differentiation-associated gene mda-7, which encodes the cyclin-dependent kinase inhibitor p21, is differentially expressed during growth, differentiation and progression in human melanoma cell. Oncogene, 10:1855–1864.
6. Jiang, H., Lin., J. J., Su, Z.-z., Goldstein, N. I., and Fisher, P. B. (1995) Substraction hybridization identifies a novel melanoma differentiation associated gene, mda-7, modulated during human melanoma differentiation, growth and progression. Oncogene, 11:2477–2486.
7. Jiang, H. Su, Z.-z., Lin, J. J., Goldstein, N. I., Young C. S. H., and Fisher, P. B. (1996). The melanoma differentiation associated gene mda-7 suppresses cancer cell growth. Proc. Natl. Acad. Sci. USA, 93:9160–9165.
8. Su, Z.-z., Madireddi, M. T., Lin, J. J., Young, C. S. H., Kitada, S., Reed, J. C., Goldstein, N. I. and Fisher, P. B. (1997) The cancer growth suppressor gene mda-7 selectIvely induces apoptosis in human cancer cells and inhibits tumor growth in nude mice. In preparation.

What is claimed is:

1. An isolated mda-9 gene having the nucleotide sequence shown in SEQ ID NO:1.

2. An antisense oligonucleotide that specifically hybridizes to an mRNA encoded by the protein-coding region of a gene encoding SEQ ID NO:2.

3. An antisense oligonucleotide that specifically hybridizes to the promoter of the isolated gene of claim 1.

4. An antisense oligonucleotide that specifically hybridizes to an mRNA encoded by the protein-coding region of the gene of claim 1.

5. A composition comprising an amount of the oligonucleotide of any one of claims 2, 3 or 4 and a pharmaceutically acceptable carrier.

6. The composition of claim 5, further comprising a substance which facilitates delivery of said oligonucleotide into a cell.

7. The composition of claim 6, wherein the substance is a liposome or an antibody.

8. The composition of claim 6, wherein the oligonucleotide is delivered into the cell by a viral vector.

9. An isolated nucleic acid molecule comprising a nucleotide sequence beginning with the Adenine at position 76 and ending with Adenine at position 972 of SEQ ID NO:1.

* * * * *

UNITED STATES PATENT AND TRADEMARK OFFICE
CERTIFICATE OF CORRECTION

| | | |
|---|---|---|
| PATENT NO. | : 6,548,650 B1 | Page 1 of 1 |
| APPLICATION NO. | : 09/345883 | |
| DATED | : April 15, 2003 | |
| INVENTOR(S) | : Paul B. Fisher | |

It is certified that error appears in the above-identified patent and that said Letters Patent is hereby corrected as shown below:

On page 1, Column 1, line 11-14, please delete and insert the following header and paragraph:

--Statement Regarding Federally Sponsored Research or Development
This invention was made with government support under grant number CA35675 awarded by the National Cancer Institute. The government has certain rights in the invention.--

Signed and Sealed this
Thirtieth Day of October, 2012

David J. Kappos
*Director of the United States Patent and Trademark Office*